(12) United States Patent
Gunzinger et al.

(10) Patent No.: US 7,875,631 B2
(45) Date of Patent: Jan. 25, 2011

(54) TETRAHYDROISOQUINOLINE-AND TETRAHYDROBENZAZEPINE DERIVATIVES AS IGF-1 R INHIBITORS

(75) Inventors: Jan Gunzinger, Couvet (CH); Kurt Leander, Peseux (CH)

(73) Assignee: Analytecon S.A., Couvet (CH)

( * ) Notice: Subject to any disclaimer, the term of this patent is extended or adjusted under 35 U.S.C. 154(b) by 1088 days.

(21) Appl. No.: 10/591,174

(22) PCT Filed: Mar. 12, 2004

(86) PCT No.: PCT/CH2004/000147

§ 371 (c)(1),
(2), (4) Date: Aug. 30, 2006

(87) PCT Pub. No.: WO2005/087743

PCT Pub. Date: Sep. 22, 2005

(65) Prior Publication Data

US 2007/0129399 A1 Jun. 7, 2007

(51) Int. Cl.
C07D 217/02 (2006.01)
A61K 31/47 (2006.01)
(52) U.S. Cl. .................. 514/310; 514/213.01; 540/593; 546/146
(58) Field of Classification Search ........................ None
See application file for complete search history.

(56) References Cited

U.S. PATENT DOCUMENTS 4,349,472 A 9/1982 Gold et al.
6,337,338 B1 1/2002 Kozlowski et al.

FOREIGN PATENT DOCUMENTS

| EP | 1 113 007 A | 7/2001 |
|---|---|---|
| WO | WO 02/102804 A1 | 12/2002 |
| WO | WO 02/102805 A1 | 12/2002 |
| WO | WO 03/048133 A | 6/2003 |
| WO | WO 03/100059 A2 | 12/2003 |

OTHER PUBLICATIONS

Carlos L. Arteaga et al., "Growth Inhibition of Human Breast Cancer Cells in Vitro with an Antibody Against the Type I Somatomedin Receptor", *Cancer Res.*, vol. 49, pp. 6237-6241 (Nov. 15, 1989).
D. D. De Leon et al., "Effects of Insulin-Like Growth Factors (IGFs) and IGF Receptor Antibodies on the Proliferation of Human Breast Cancer Cells", *Growth Factors*, vol. 6, pp. 327-336 (1992).
David W. Andrews et al., "Results of a Pilot Study Involving the Use of an Antisense Oligooxynucleotide Directed Against the Insulin-Like Growth Factor Type I Receptor in Malignant Astrycytomas", *J. Clin. Onc.*, vol. 19, No. 8, pp. 2189-2200 (Apr. 15, 2001).
P.J. White et al., "Antisense Inhibition of IGF Receptor Expression in HaCaT Keratinocytes: A Model for Antisense Strategies in Keratinocytes", *Antisense & Nuc. Acid Drug Dev.*, vol. 10, pp. 195-203 (2000).

Diane Prager et al., "Dominant negative inhibition of tumorigenesis in vivo by human insulin-like growth factor I receptor mutant", *Proc. Natl. Acad. Sci. USA*, vol. 91, pp. 2181-2185 (Mar. 1994).
Krysztof Reiss et al., "Inhibition of Tumor Growth by a Dominant Negative Mutant of the Insulin-Like Growth Factor I Receptor with a Bystander Effect", *Clin. Cancer Res.*, vol. 4, pp. 2647-2655 (Nov. 1998).
Laura K. Shawver et al., "Receptor Tyrosine kinases as targets for inhibition of angiogenesis", *DDT*, vol. 2, No. 2, (Feb. 1997).
Jane Pritchard et al., "Synovial Fibroblasts from Patients with Rheumatoid Arthritis, Like Fibroblasts from Graves' Disease, Express High Levels of IL-16 When Treated with Igs against Insulin-Like Growth Factor-1 Receptor", *J. Immun.*, pp. 3564-3569 (2004).
A.J. Salisbury et al., "Development of Molecular Agents for IGF Receptor Targeting", *Horm. Metab. Res.*, vol. 35, pp. 843-849 (2003).
Constantine S. Mitsiades et al., "Inhibition of the insulin-like growth factor receptor-1 tyrosine kinase activity as a therapeutic strategy for multiple myeloma, other hematologic malignancies, and solid tumors", *Cancer Cell*, vol. 5, pp. 221-230 (Mar. 2004).
Ji Sun Lee et al., "Synthesis of 1,2,3,4-Tetrahydroisoquinoline-2-sulfonic Acids," *Bull Korean Chem. Soc.*, vol. 24, No. 7, pp. 1041-1044 (2003).
T.E. Adams et al., "Structure and function of the type 1 insulin-like growth factor receptor," *CMLS Cell Mol. Life Sci.*, vol. 57, pp. 1050-1093 (2000).
Renato Baserga et al., "The IFG-I receptor in cell growth, transformation and apoptosis," *Biochimica et Biophysica Acta*, vol. 1332, pp. F105-F126 (1997).
Thea Kalebic et al., "In Vivo Treatment with Antibody against IFG-1 Receptor Suppresses Growth of Human Rhabdomyosarcoma and Down-Regulates $p34^{cdc2}$," *Cancer Research*, vol. 54, pp. 5531-5534 (Nov. 1, 1994).
Mariana Resnicoff et al., "Rat Glioblastoma Cells Expressing an Antisense RNA to the Insulin-like Growth Factor-1 (IGF-1) Receptor Are Nontumorigenic and Induce Regression of Wild-Type Tumors," *Cancer Research*, vol. 54, pp. 2218-2222 (Apr. 15, 1994).

(Continued)

*Primary Examiner* — Zinna N Davis
(74) *Attorney, Agent, or Firm* — Harness, Dickey & Pierce, P.L.C.

(57) ABSTRACT

Compounds of the formula (I): where R2, R5, R6 have the meanings as given in the description, and U, V and W, respectively, may be CR2', CR4' and CR6', respectively (with the definitions of R2', R4' and R6' again as in the description), or may be N, were synthesized. They were found to down-regulate or inhibit the expression or function of the IGF-1 receptor.

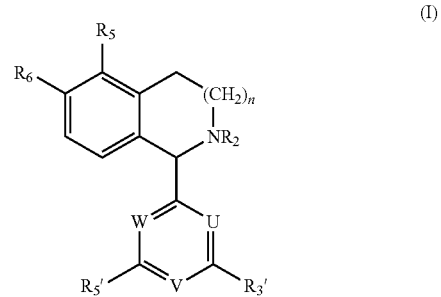

(I)

21 Claims, No Drawings

OTHER PUBLICATIONS

Consuelo D'Ambrosio et al., "A Soluble Insulin-like Growth Factor I Receptor That Induces Apoptosis of Tumor Cells in Vivo and Inhibits Tumorigenesis," *Cancer Research*, vol. 56, pp. 4013-4020 (Sep. 1, 1996).

Frauke Rininsland et al., "Suppression of insulin-like growth factor type I receptor by a triple-helix strategy inhibits IGF-I transcription and tumorigenic potential of rat C6 glioblastoma cells," *Proc. Natl. Acad. Sci. USA*, vol. 94, pp. 5854-5859 (May 1997).

Keiichiro Nakamura et al., "Down-Regulation fo the Insulin-like Growth Factor I Receptor by Antisense RNA Can Reverse the Transformed Phenotype of Human Cervical Cancer Cell Lines," *Cancer Research*, vol. 60, pp. 760-765 (Feb. 1, 2000).

Christopher J. Wraight et al., "Reversal of epidermal hyperproliferation in psoriasis by insulin-like growth factor I receptor antisense oligonucleotides," *Nature Biotechnology*, vol. 18, pp. 521-526 (May 2000).

Antoni Bayes-Genis et al., "The Insulin-Like Growth Factor Axis a Review of Atherosclerosis and Restenosis," *Circulation Research*, pp. 125-130 (Feb. 4, 2000).

Li Long et al., "Loss of the Metastatic Phenotype in Murine Carcinoma Cells Expressing an Antisense RNA to the Insulin-like Growth Factor Receptor," *Cancer Research*, vol. 55, pp. 1006-1009 (Mar. 1, 1995).

Renato Baserga, "Controlling IGF-receptor function: a possible strategy for tumor therapy," *BTECH*, vol. 14, pp. 150-152 (1996).

Renato Baserga et al., "The IGF-I Receptor and Cancer," *Endocrine*, vol. 7, No. 1, pp. 99-102 (Aug. 1997).

V.M. Macauley et al., "Downregulation fo the type 1 insulin-like growth factor receptor in mouse melanoma cells is associated with enhanced radiosensitivity tivity and impaired activation of Atm kinase," *Oncogene*, vol. 20, pp. 4029-4040 (2001).

Marcelina Parrizas et al., Specific Inhibition of Insulin-Like Growth Factor-1 and Insulin Receptor Tyrosine Kinase Activity and Biological Function by Tyrphostins, *Endocrinology*, vol. 138, No. 4, pp. 1427-1433 (1997).

Galia Blum et al., "Substrate Competitive Inhibitors of IGF-I Receptor Kinase," *Biochemistry*, vol. 39, No. 51, pp. 15705-15712 (2000).

Galia Blum et al., "Development of New Insulin-like Growth Factor-1 Receptor Kinase Inhibitors Using Catechol Mimics," *J. Biological Chemistry*, vol. 278, No. 42, pp. 40442-40454 (Oct. 17, 2003).

Lena Kanter-Lewensohn et al., "Tamoxifen-induced cell death in malignant melanoma cells: possible involvement of the insulin-like growth factor-1 (IGF-1) pathway," *Molecular and Cellular Endocrinology*, vol. 165, pp. 131-137 (2000).

Akira Akahori et al., "Cytotoxic Agents of Thujopsis dolabrata (L. fil.) Sieb et Zucc." *Chem. Pharm. Bull.*, vol. 20, No. 6, pp. 1150-1155 (1972).

Masahiko Kohno et al., "Synthesis of Phenethylamines by Hydrogenation of β-Nitrostyrenes," *Chem. Soc. of Japan*, vol. 63, No. 4, pp. 1252-1254 (1990).

Stephen A DiBiase et al., "Direct Synthesis of α,β-Unsaturated Nitriles from Acetonitrile and Carbonyl Compounds: Survey, Crown Effects, and Experimental Conditions," *J. Org. Chem*, vol. 44, No. 25, pp. 4640-4649 (1979).

Melvin Euerby et al., "A Convenient Synthesis of 3-Methylthiobenzaldehyde," *Synthetic Communications*, vol. 11, No. 10, pp. 849-851 (1981).

Makoto Ando et al., "Catalytic Activities of Salicylaldehyde Derivatives, VI.1) Syntheses of Some Dimethylsulfionio Derivatives of Salicylaldehyde," *Bull. of the Chem. Soc. of Japan*, vol. 51, No. 8, pp. 2435-2436 (1978).

Michael J. Munchhof et al., "A Novel Route to Chiral, Nonracemic 1-Alkyl- and 1-Aryl-Substituted Tetrahydroisoquinolines. Synthesis of (−)Salsolidine and (+)-Cryptostyline II," *J. Org. Chem.*, vol. 60, pp. 7086-7087 (1995).

Richard P. Polniaszek et a., "Stereoselective Reductions of Chiral Iminium Ions," *Tetrahedron Letters*, vol. 28, No. 39, pp. 4511-4514 (1997).

Nobuyuki Uematsu et al., "Asymmetric Transfer Hydrogenation of Imines," *J. Am. Chem. Soc.*, vol. 118, pp. 4916-4917, (1996).

Gerrit J. Meuzelaar et al., "Chemistry of Opium Alkaloids, 45[1][‡1] Improvements in the Total Synthesis of Morphine," *Eur. J. Org. Chem.*, pp. 2315-2321, (1999).

Conly L. Rieder et al., "Microtubule disassembly delays the G2-M transition in vertebrates," *Current Biology*, vol. 10, No. 17, pp. 1067-1070, (Aug. 2000).

Michele Rubini et al., "The IGF-I Receptor in Mitogenesis and Transformation of Mouse Embryo Cells: Role of Receptor Number," *Experimental Cell Research*, vol. 230, pp. 284-292 (1997).

Minor et al., "Synthesis and Molecular Modeling of 1-Phenyl-1,2,3,4-tetrahydroisoquinolines and Related 5,6,7,8,9-Tetrahydro-13b*H*-dibenzo[*a,h*]quinolines as D$_1$ Dopamine Antagonists", J. Med. Chem. vol. 37, pp. 4317-4328 (1994).

TETRAHYDROISOQUINOLINE- AND TETRAHYDROBENZAZEPINE DERIVATIVES AS IGF-1 R INHIBITORS

FIELD OF THE INVENTION

The present invention relates to novel compounds capable of down-regulating or inhibiting the expression or function of the insulin-like growth factor-1 receptor (IGF-1R). The invention is also directed to methods of down-regulating or inhibiting IGF-1R expression or function in order to prevent and/or treat cancer and other abnormal cell growth, and metabolic as well as blood vessel proliferate disorders, in which uncontrolled expression of this receptor is observed.

BACKGROUND OF THE INVENTION

The insulin-like growth factor receptor (IGF-1R) is one of 58 trans-membrane tyrosine kinase receptors present in humans [Review: Structure and function of the Type 1 insulin-like growth factor receptor. T. E. Adams et al. Cell. Mol. Life Sci. 57 (2000) 1050-1093]. Genetic evidence and studies on cells lacking the IGF-1 receptor have demonstrated that it is required for optimal growth, but not an absolute condition for growth [Baserga et al. Biochim. Biophys. Acta 1332(1997) 105-126]. An expression of the IGF-1 receptor protects cells from apoptosis and seems to be a requirement for the establishment and maintenance of the transformed phenotype both in vitro and in vivo [R. Baserga et al. Biochim. Biophys. Acta 1332 (1997) 105-126]. Several in vitro and in vivo studies have demonstrated that inhibition of the expression or function of the IGF-1 receptor reverses the transformed phenotype and inhibits tumor cell growth. The techniques used in these studies include neutralizing antibodies [Kalebic et al. Cancer Res. 54(1994) 5531-5534], anti-sense oligonucleotides [Resnicoff et al. Cancer Res. 54(1994) 2218-2222], dominant negative receptors [D'Ambrosio et al. Cancer Res. 56(1996) 4013-4020], triple-helix forming oligonucleotides [Rinninsland et al. Proc.Natl. Acad. Sci. 94(1997) 5854-5859], antisense mRNA [Nakamura et al. Cancer Res. 60(2000) 760-765] and RNA interference using a double stranded RNA (V. M. Macaulay et al. WO-A-03/100059).

The use of antisense oligonucleotides to inhibit the IGF-1 receptor expression in keratinocytes has been shown to reverse the epidermal hyper proliferation in psoriasis lesions [C. J. Wraight et al. Nat. Biotechnol. 18(2000) 521-526].

Down-regulation of the IGF-1 receptor would possibly also have beneficial effect with respect to diseases such as diabetic retinopathy [L. K. Shawver et al. DDT 2(1997) 50-63] as well as atherosclerosis and restenosis [A. Bayes-Genis et al. Circ. Res. 86(2000) 125-130].

The IGF-1 receptor system is regarded as an attractive target in the prevention and/or treatment of diseases that are dependant on an expression or over-expression of the IGF-1 receptor for their proliferation [L. Long et al. Cancer Research 55(1995) 1006-1009, R. Baserga TIBTECH 14(1996) 150-152; R. Baserga et al. Endocrine 7 (August 1997) 99-102; V. M. Macaulay et al. Annals of Oncogene 20 (2001) 4029-4040].

A series of substances, named tyrphostins, have been claimed to down-regulate or inhibit the expression of the IGF-1 receptor [M. Parrizas et al. Endocrinology 138 (1997) 1427-1433; G. Blum et al. Biochemistry 39(2000) 15705-15712; G. Blum et al. J. Biol. Chem. 278 (2003) 40442-404541]. The drawback with the tyrphostins are their low activity in cell systems and that they cross-react with the insulin receptor.

It has been demonstrated [L. Kanter-Lewensohn et al. Mol. Cell. Endocrinology 165 (2000) 131-137] that tamoxifen, at high concentration, has the ability to down-regulate or inhibit the tyrosine phosphorylation of the IGF-1R β-subunit, thereby blocking downstream signalling.

In U.S. Pat. No. 6,337,338 b1, a number of heteroaryl-aryl urea substances-are described as antagonists of the IGF-1 receptor. In cell growth inhibition studies on MCF-7 and MCF-10 cell lines the substances showed low activities.

In the patent publication WO 02/102804 A1 it is demonstrated that podophyllotoxin, deoxypodophyllotoxin, picropodophyllin and deoxypicropodophyllin are selective and efficient inhibitors of the IGF-1 receptor. Deoxypicropodophyllin has previously [A. Akahori et al. Chem. Pharm. Bull. 20(1972) 1150-1155] been shown to be superior to deoxypodophyllotoxin in retarding the death of mice inoculated with lymphatic leukemia L1210. No mechanism of action, however, was proposed.

In the patent publication WO 02/102805 A1 it is shown that also acetylpodophyllotoxin, epipodophyllotoxin, podophyllotoxone and 4'-demethylpodophyllotoxin are potent inhibitors of the IGF-1R phosphorylation.

In the patent publication WO 03/048133 A1 a number of pyrimidine derivatives are described as modulators of the IGF-1 receptor.

The present invention aims to provide compounds with improved IGF-1R down-regulating activity.

SUMMARY OF THE INVENTION

The object set is achieved by the compounds of the following formula (I):

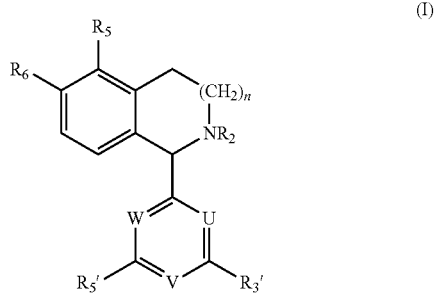

wherein $R_2$ designates hydrogen, Me, Et, CHO, CN, OH, OMe, $COR_9$, $COOR_9$, $CONHR_9$ or $CSNHR_9$, whereby $R_9$ denotes $(C_1-C_4)$alkyl;

$R_5$ designates hydrogen, $(C_1-C_4)$alkyl, OH, $(C_1-C_4)$alkoxy, $OCF_3$, trifluoromethyl or halogen;

$R_6$ designates Me, $(C_1-C_4)$alkoxy, $OCF_3$, SMe or SEt;

n is 1 or 2;

$R_3'$ and $R_5'$ each independently designate OH, Me, Et, OMe, $OCF_3$, trifluoromethyl or halogen;

U designates N or $CR_2'$, whereby $R_2'$ denotes hydrogen, $(C_1-C_4)$alkyl, $(C_1-C_4)$alkoxy, trifluoromethyl or halogen;

V designates N or $CR_4'$, whereby $R_4'$ denotes hydrogen, $C_1-C_6)$alkoxy, $(C_1-C_6)$alkyl, OH, trifluoromethyl or halogen;.

W designates N or $CR_6'$, whereby $R_6'$ denotes hydrogen, $(C_1-C_4)$alkyl, $(C_1-C_4)$alkoxy, trifluoromethyl or halogen;

and pharmaceutically acceptable salts thereof, where applicable (see below).

Preferred embodiments of the compound (I) are derivable from the dependent claims. The most preferred examples of compounds of formula (I) are those of claim 13.

Further objects of the invention are the use of the compounds (I) as a medicament, particularly for the prevention or treatment of diseases in which the down-regulation or inhibition of the expression or function of the IGF-1 receptor is considered beneficial, and pharmaceutical compositions containing a compound (I).

DETAILED DESCRIPTION OF THE INVENTION

The compounds of formula (I) contain a tetrahydroisoquinoline moiety (n=1) or a tetrahydrobenzazepine moiety (n=2).

In the above formula (I) preferably $R_2$ is Me, OH, CN, CHO, $COR_9$ or $COOR_9$; Particularly preferred examples of $R_2$ are Me (methyl), CHO (formyl), COMe (acetyl) and CN (cyano).

Preferably $R_5$ is hydrogen, Me, OMe or halogen; and preferably $R_6$ is OMe or OEt. Particularly preferably $R_5$ is hydrogen or OMe and $R_6$ is OMe. The most preferred substituent pattern for $R_5$ and $R_6$ is $R_5$ =hydrogen and $R_6$=OMe.

In formula (I) the substituent on the 1-position of the 1,2,3,4-tetrahydroisoquinoline or 2,3,4,5-tetrahydro-1H-2-benzazepine moieties may be a phenyl substituent (U=$CR_2'$; V=$CR_4'$; W=$CR_6'$), a 4-pyridyl substituent (U=$CR_2'$; V=N; W=CR6'), a 2-pyridyl substituent (V=$CR_4'$; U=N, W=$CR_6'$, or U=$CR_2'$, W=N), a 2-pyrimidyl substituent (U, W=N; V=$CR_4'$), a 4-pyrimidyl substituent (V=N; U=$CR_2'$, W=N, or U=N, W=$CR_6$=), or a triazinyl substituent (U, V, W=N).

A preferred substitution pattern on said substituent on the 1-position is $R_3'$, $R_5$=each independently chloro, bromo, Me or OMe. In one more preferred embodiment $R_3'$ and $R_5'$ are identical. In another preferred embodiment they are both chloro, both bromo, both Me or both OMe; in another preferred embodiment $R_3'$ is chloro or bromo, and $R_5'$ is OMe. Most preferably both $R_3'$ and $R_5'$ are chloro or bromo. When the 1-substituent is phenyl then $R_2'$ and $R_6'$ are preferably hydrogen. $R_4'$ then is preferably hydrogen, chloro, bromo, Me or OMe. Three most preferred substitution patterns on the phenyl as the 1-substituent are a) $R_3'$, $R_4'$, $R_5'$=OMe; b) $R_3'$=chloro, $R_4'$, $R_5'$=OMe; and c) $R_4'$=hydrogen and $R_3'$ and $R_5'$=both chloro or both bromo. Due to the rotational freedom of the phenyl, in b) the definitions for $R_3'$ and $R_5'$ are interchangeable.

The alkyl residue in the $(C_1-C_4)$alkyl or $(C_1-C_4)$alkoxy, as used in the substituent definitions of formula (I), may be branched, unbranched or cyclic and may contain double or triple bonds. It is e.g. methyl, ethyl, n-propyl, n-butyl, isopropyl, sec-butyl, t-butyl, cyclopropyl, cyclobutyl, ethenyl, prop-2-enyl or prop-3-enyl, but-1-enyl, but-2-enyl, but-3-enyl or propargyl. Preferably it is methyl, ethyl or isopropyl; particularly preferably it is methyl.

The alkyl residue in the $(C_1-C_6)$alkyl or $(C_1-C_6)$alkoxy may be unbranched, branched or cyclic and may contain double or triple bonds. Examples of unbranched alkyls are methyl, ethyl, n-propyl, n-butyl, n-pentyl and n-hexyl. Examples of branched-alkyl are isopropyl, sec-butyl, t-butyl, (1,1-di-ethyl)methyl, (1-propyl-1-methyl)methyl, (1-isopropyl-1-methyl)methyl, (1,1-dimethyl-1-ethyl)methyl, (1-t-butyl)methyl, (1-propyl-1-ethyl)methyl, (1-isopropyl-1-ethyl)methyl, (1,1-diethyl-1-methyl)methyl and (1-t-butyl-1-methyl)methyl. Examples of the cyclic alkyl are cyclopropyl, cyclobutyl, cyclopentyl, cyclohexyl or (2- or 3-methyl)cyclopentyl. Examples of unsaturated alkyls are ethenyl, prop-2-enyl, but-1-enyl, but-2-enyl, but-3-enyl, pent-1-enyl, pent-2-enyl, pent-3-enyl, pent-4-enyl, penta-1,3-dienyl, penta-1,4-dienyl, penta-2,4-dienyl or propargyl.

The term "halogen" means in the context of the present application fluoro, chloro or bromo.

In the context of the present application the term "IGF-1 receptor" encompasses human IGF-1 receptor, the amino acid sequence of which is known [see e.g. T. E. Adams et al. Cellular and Molecular Life Sciences 2000, 57, p. 1050-1093], but it also encompasses other IGF-1R, such as IGF-1R of mammals in general.

The pharmaceutically acceptable salts of the compounds of formula (I) are acid addition salts with pharmaceutically acceptable acids, which are possible in the case where $R_2$ is hydrogen, Me or Et; and/or at least one of U, V and W is nitrogen. Examples of pharmaceutically acceptable acids are hydrochloric, hydrobromic, methanesulfonic, acetic, propionic, benzoic, citric, tartaric, malic, maleic, fumaric, lactic, nitric, phosphoric or succinic acid.

The compounds (I) of the present invention can be prepared using the methods described below, with reference to schemes 1a and 1b. Preferably the compounds (I) of the present invention are synthesized via the imine (II), which is a 3,4-dihydroisoquinoline (n=1) or a 4,5-dihydro-3H-2-benzazepine (n=2). The imine (II) may then be converted by reduction to a secondary amino compound (I) of the invention, where $R_2$=hydrogen. As the reducing agent sodium borohydride in methanol or other reducing agents may be used, such as DI-BAL, $B_2H_6$, $LiAlH_4$, or catalytic hydrogenation using a catalyst, which may be chiral, suited for reducing imines, but which will not influence other parts of the compound (I, $R_2$=hydrogen).

The compounds (I) where $R_2$=Me or Et and the 1-substituent is phenyl, may be prepared by alkylation of (II) with a corresponding alkyl halide $R_2X$, where X is a leaving group such as bromo, iodo, mesylate, tosylate or triflate, to form an intermediate iminium salt (III) (scheme 1a). This alkylation is preferably performed at room temperature to reflux temperature, in an aprotic solvent such as acetone, DMF, $CH_3CN$, DMSO or 1,2-dimethoxyethane. The iminium salt (III) is then reduced under similar conditions as above for the reduction of the imine (II) itself, to form compounds (I) of the invention where $R_2$=Me or Et.

The compounds (I) where $R_2$=Me or Et, respectively, and the 1-substituent is other than phenyl (i.e. at least one of U, V or W is nitrogen) may be prepared by acylation of (I), where $R_2$=hydrogen, with XCOOEt or XCOMe, respectively, where X is a leaving group such as chloro (in XCOMe X may also be acetoxy), to form a compound (I) wherein $R_2$ is COOEt or COMe, respectively, which is then reduced, e.g. with Li—$AlH_4$ or $B_2H_6$, to the compound (I) with $R_2$=Me or Et, respectively (scheme 1b).

For all compounds (I), where $R_2$=methyl, the standard Eschweiler-Clarke reaction may also be used, to directly form these derivatives from the corresponding secondary amino compound (I) with $R_2$=hydrogen (scheme 1a or 1b).

All compounds (I) where $R_2$=$COR_9$, $COOR_9$ or cyano can be prepared from the above secondary amino compound (I), where $R_2$=hydrogen, by acylation with an appropriate acyl halide $R_9COX$, (in particular for $R_9$=Me also acetic anhydride may be used), haloformic acid ester $R_9OCOX$, or cyanogen halide XCN (X=chloro or bromo); by using a suited auxiliary base such as $NEt_3$ or pyridine and, optionally, a catalyst such as 4-dimethylaminopyridine (schemes 1a or 1b). The reaction temperature may be from room temperature to the boiling temperature of the solvent, which solvent may be an ether such as THF or 1,2-dimethoxyethane; $CH_3CN$; N-methylpyrrolidone or $CH_2Cl_2$. In the case a cyanogen halide is used, anhydrous potassium carbonate may be used to neutralize the formed hydrogen halide. Acetylations ($R_2$=COMe) are preferably performed in neat acetic anhydride, i.e. without solvent or catalysts, to facilitate the isolation of the N-acetyl derivative.

All compounds (I) where $R_2$=formyl, may be prepared from the above secondary amino compound (I), where $R_2$=hydrogen, by using formic acid in refluxing toluene (schemes 1a and 1b).

All compounds (I) where $R_2$=CONHR$_9$ or CSNHR$_9$ can be prepared from a secondary amino compound (I), where $R_2$=hydrogen, under standard condition by reacting this with an isocyanate OCNR$_9$ or isothiocyanate SCNHR$_9$ at room temperature in an inert solvent such as an ether, DMF or acetonitril (schemes 1a and 1b).

The imine (II) itself may be prepared from an appropriately substituted phenetylamine (VIII) or 3-phenylpropylamine (IX) (scheme 2), by acylating either of these with an appropriately substituted acyl chloride (X), e.g. under standard Schotten-Baumann conditions, which gives an amide (IV). This amide (IV) may then be cyclized to the imine (II) under dehydrating conditions with a dehydrating agent such as zinc chloride or POCl$_3$ (Bischler-Napieralski type) or $P_2O_5$ (Pictet-Gams type).

Either of the amines (VIII) or (IX) may be prepared by techniques known in the art from appropriately substituted benzaldehydes (V). For the sequence (V) to (VI) to (VIII) reference is made e.g. to Kohno et al., Bull. Chem. Soc. Jpn., 1990, 63(4), 1252-1254. In some cases the phenethyl amine (VIII) is even commercially available, as is the case Scheme 1a

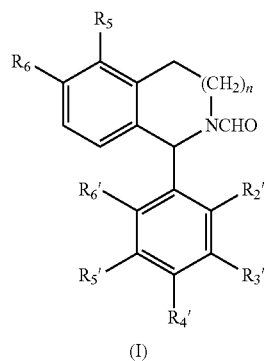

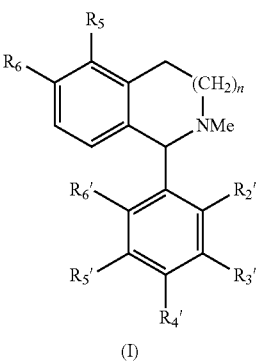

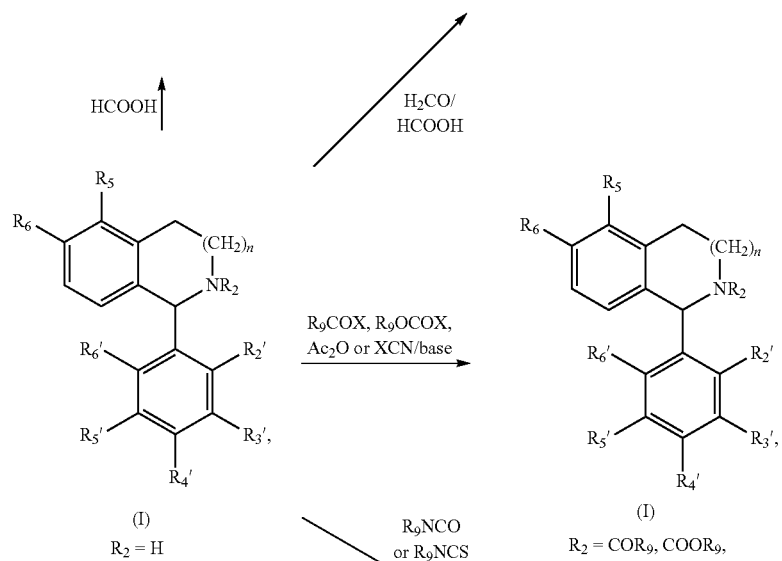

-continued
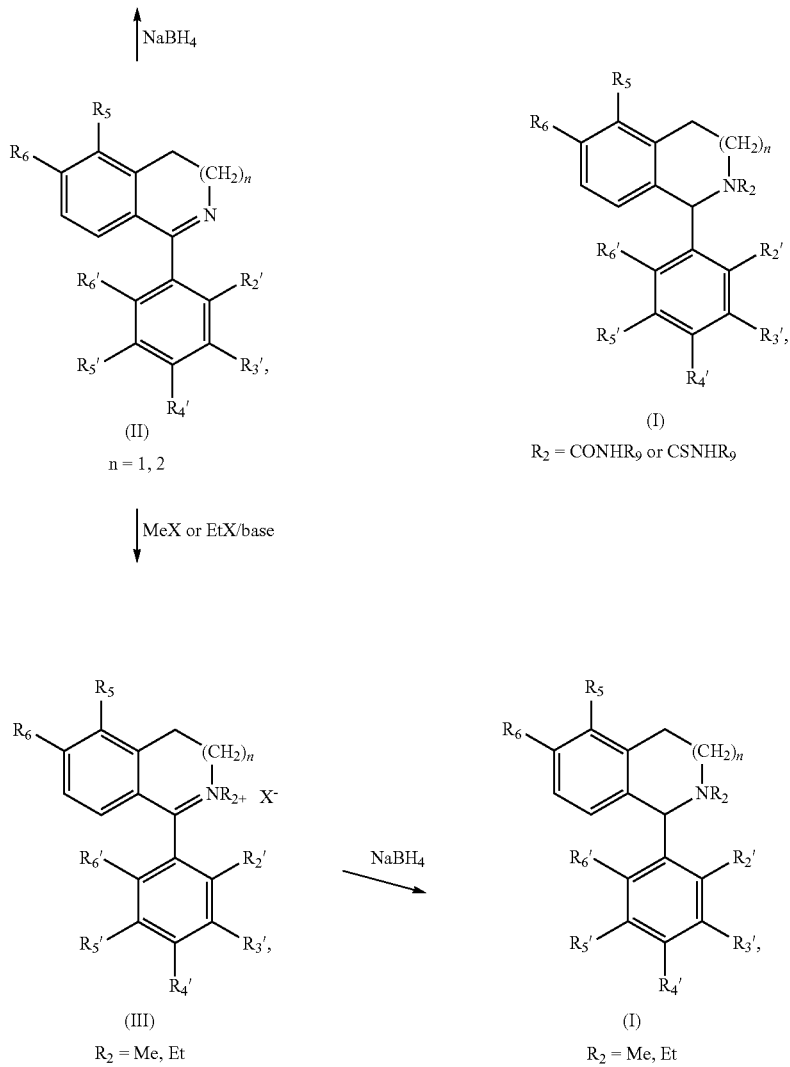
Scheme 1b
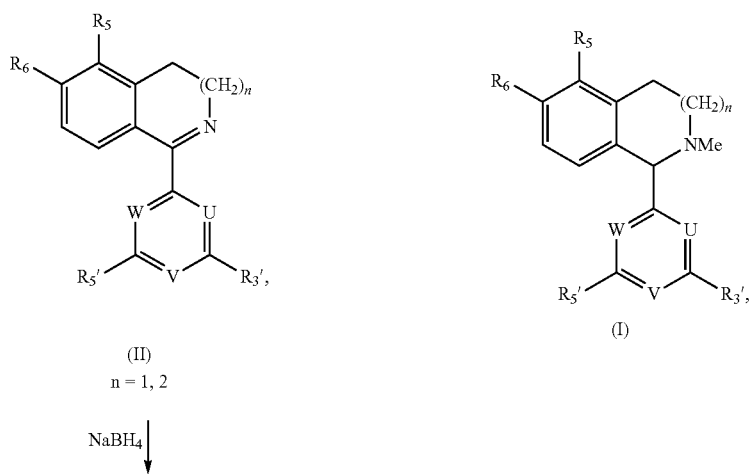

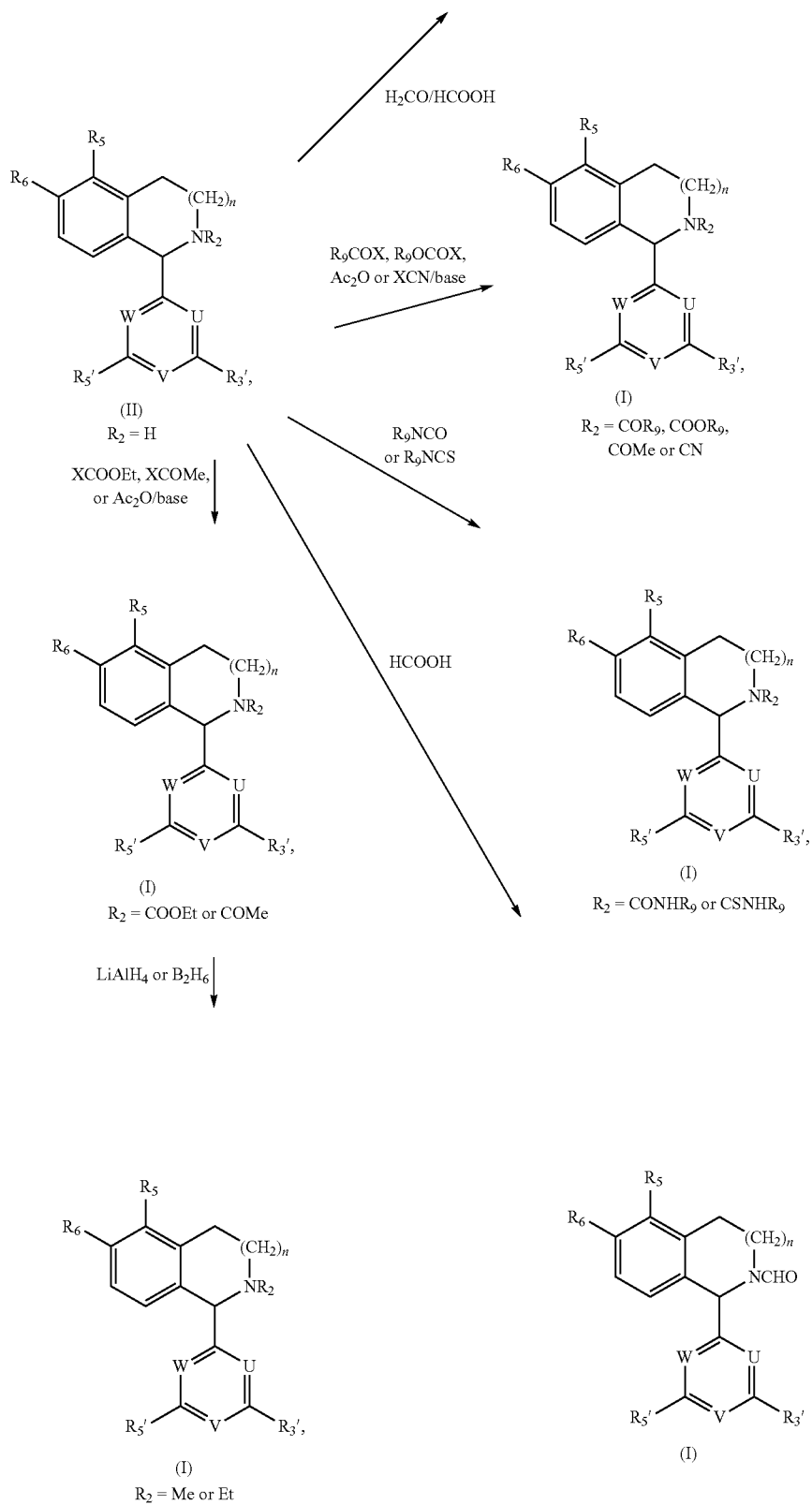

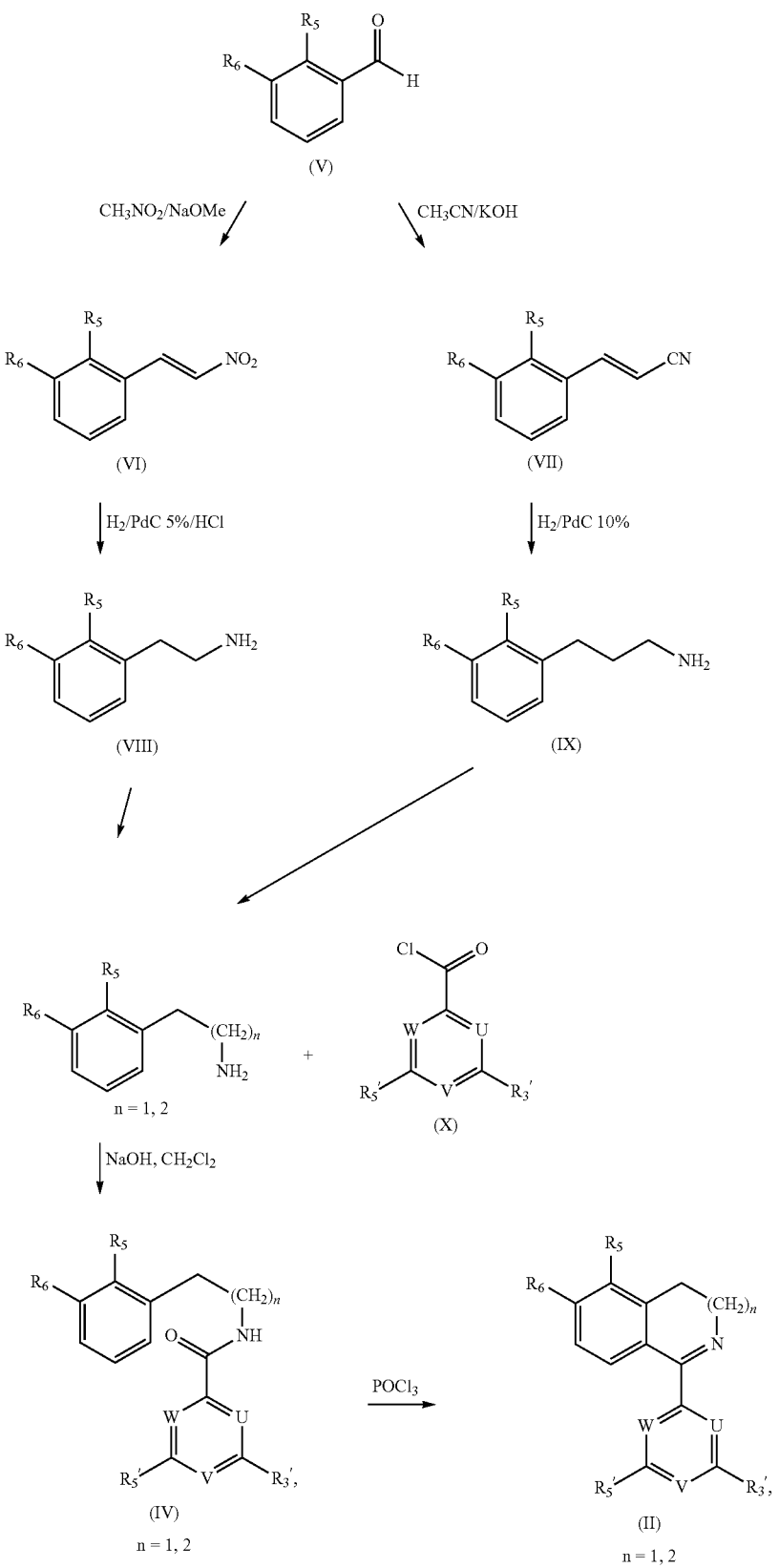

for 3-methoxyphenylethylamine, which inter alia was used in examples 31-38 (see below). The sequence (V) to (VII) is easily achieved in accordance with the procedure devised for the corresponding 4-methoxy derivative (DiBiase, S. A. et al. J.Org.Chem. 44(1979) 4640-4649). Compound (VII) is there-after reduced to the amine (IX) by catalytic hydrogenation. The appropriately substituted benzaldehyde (V) of scheme 2 in turn is either commercially available or known from the literature.

Some examples of known benzaldehydes (V) that may be used for synthesizing some preferred compounds (I) are the following:

| benzaldehyde (V) | CAS reg. no. |
|---|---|
| 3-methoxybenzaldehyde | 591-31-1 |
| 2-fluoro-3-methoxybenzaldehyde | 103438-88-6 |
| 2-chloro-3-methoxybenzaldehyde | 54881-49-1 |
| 2-bromo-3-methoxybenzaldehyde | 10401-18-0 |
| 2-hydroxy-3-methoxybenzaldehyde | 148-53-8 |
| 3-ethoxybenzaldehyde | 22924-15-8 |
| 2-chloro-3-ethoxybenzaldehyde | 99586-82-0 |
| 3-ethoxy-2-hydroxybenzaldehyde | 492-88-6 |
| 2-chloro-3-methylbenzaldehyde | 61563-28-8 |
| 2-bromo-3-methylbenzaldehyde | 109179-31-9 |
| 3-isopropoxybenzaldehyde | 75792-33-5 |
| 2-hydroxy-3-propyloxybenzaldehyde | 222031-84-7 |
| 3-butyloxy-2-hydroxybenzaldehyde | 91849-57-9 |
| 2-hydroxy-3-isobutyloxybenzaldehyde | 222031-85-8 |
| 2-hydroxy-3-isopropoxybenzaldehyde | 222031-87-0 |
| 3-methylbenzaldehyde | 620-23-5 |
| 2-hydroxy-3-methylbenzaldehyde | 824-42-0 |
| 2,3-dimethoxybenzaldehyde | 86-51-1 |
| 2,3-diethoxybenzaldehyde | 24454-82-8 |
| 2-ethoxy-3-methoxybenzaldehyde | 66799-97-1 |
| 3-ethoxy-2-methoxybenzaldehyde | 75792-34-6 |
| 3-isopropoxy-2-methoxybenzaldehyde | 218903-24-3 |
| 2-methoxy-3-methylbenzaldehyde | 67639-61-6 |
| 2-ethoxy-3-methylbenzaldehyde | 532965-62-1 |
| 3-methoxy-2-methylbenzaldehyde | 56724-03-9 |
| 3-hydroxy-2-ethylbenzaldehyde | 532966-36-2 |
| 3-methoxy-2-propylbenzaldehyde | 97582-12-2 |
| 2-isopropyl-3-methoxybenzaldehyde | 93351-17-8 |
| 2-butyl-3-methoxybenzaldehyde | 151038-64-1 |
| 2-(1,1-dimethylethyl)-3-methoxybenzaldehyde | 151038-66-3 |
| 3-(trifluoromethoxy)benzaldehyde | 52771-21-8 |
| 3-hydroxy-2-methoxybenzaldehyde | 66495-88-3 |
| 3-hydroxy-2-ethoxybenzaldehyde | 182067-51-2 |
| 3-hydroxy-2-propoxybenzaldehyde | 508202-83-3 |
| 3-(methylthio)benzaldehyde | 73771-35-4 |
| 3-(ethylthio)benzaldehyde | 87425-00-1 |
| 3-bromo-2-fluorobenzaldehyde | 149947-15-9 |
| 2-fluoro-3-hydroxybenzaldehyde | 103438-86-4 |
| 2-chloro-3-hydroxybenzaldehyde | 56962-10-8 |
| 2-bromo-3-hydroxybenzaldehyde | 196081-71-7 |
| 3-hydroxybenzaldehyde | 100-83-4 |
| 3-hydroxy-2-methylbenzaldehyde | 90111-15-2 |
| 3-hydroxy-2-propylbenzaldehyde | 532966-38-4 |
| 3-hydroxy-2-isopropylbenzaldehyde | 532966-40-8 |
| 2-butyl-3-hydroxybenzaldehyde | 532966-42-0 |
| 2-(1,1-dimethylethyl)-3-hydroxybenzaldehyde | 532966-46-4 |
| 3-hydroxy-2-(1-methylpropyl)benzaldehyde | 532966-44-2 |
| 2-hydroxy-3-trifluoromethoxybenzaldehyde | 497959-31-6 |
| 2-hydroxy-3-(methylthio)benzaldehyde | 67868-82-0 |
| 3-benzyloxy-2-hydroxybenzaldehyde | 86734-59-0 |

2-($C_1$-$C_4$)alkyl-3-($C_1$-$C_4$)alkoxybenzaldehydes (i.e. with $R_5$=($C_1$-$C_4$)alkyl, $R_6$=($C_1$-$C_4$)alkoxy) and 2-($C_1$-$C_4$)alkyl-3-trifluoromethoxy-benzaldehydes (i.e. with $R_5$=($C_1$-$C_4$) alkyl, $R_6$=$OCF_3$), respectively, may be synthesized from 2-($C_1$-$C_4$)alkyl-3-hydroxy-benzaldehydes by Williamson etherification with a corresponding ($C_1$-$C_4$)alkyl bromide and trifluoromethyliodide, respectively.

2-($C_1$-$C_4$)alkoxy-3-($C_1$-$C_4$)alkoxybenzaldehydes (i.e. with $R_5$=($C_1$-$C_4$)alkoxy, $R_6$=($C_1$-$C_4$)alkoxy) and 2-($C_1$-$C_4$)alkoxy-3-trifluoromethoxy-benzaldehydes (i.e. with $R_5$=($C_1$-$C_4$)alkoxy, $R_6$=$OCF_3$), respectively, may be synthesized from 2-($C_1$-$C_4$) alkoxy-3-hydroxy-benzaldehydes by Williamson etherification with a corresponding ($C_1$-$C_4$) alkyl bromide and trifluoromethyliodide, respectively. Alternatively all these compounds are available from 3-benzyloxy-2-hydroxybenzaldehyde by etherification, followed by debenzylation and etherification f the 3-hydroxy group.

2-($C_1$-$C_4$)alkyl-3-methylthio-benzaldehydes (i.e. with $R_5$=($C_1$-$C_4$)alkyl, $R_6$=SMe) and 2-($C_1$-$C_4$)alkyl-3-ethylthio-benzaldehydes (i.e. with $R_5$=($C_1$-$C_4$)alkyl, $R_6$=SEt), respectively, may be synthesized from 2-($C_1$-$C_4$)alkyl-3-bromo-benzaldehyde diethyl acetals by reacting its Grignard reagent with dimethyl sulfide or diethyl sulfide, respectively (for a similar reaction see M. Euerby et al., Synthetic Communications 11 (1981), 849-851).

2-($C_1$-$C_4$)alkoxy-3-methylthio-benzaldehydes (i.e. with $R_5$=($C_1$-$C_4$)alkoxy, $R_6$=SMe) and 2-($C_1$-$C_4$)alkoxy-3-ethylthio-benzaldehydes (i.e. with $R_5$=($C_1$-$C_4$)alkoxy, $R_6$=SEt), respectively, may be synthesized from 2-($C_1$-$C_4$) alkoxy-3-bromo-benzaldehydes by reacting its Grignard reagent with dimethyl sulfide or diethyl sulfide, respectively (for a similar reaction see M. Euerby et al., Synthetic Communications 11 (1981), 849-851). Another route to these starting materials is by etherification of 2-hydroxy-3-(methylthio)benzaldehyde or 2-hydroxy-3-(ethylthio)benzaldehyde (A. Makoto et al. Bull. Chem. Soc. Jpn. 51 (1978) 2435-2436).

The appropriately substituted acyl chlorides (X) for the synthesis of the amide (IV) are benzoyl chlorides, when U=$CR_2'$, V=$CR_4'$ and W=$CR_6'$; and are known or can be synthesized under standard conditions from corresponding benzoic acids with thionyl chloride or oxalyl chloride. Some examples of known benzoyl chlorides (X) and benzoic acids that may be used for synthesizing some preferred compounds (I) are the following:

| benzoyl chloride (X) | CAS No. |
|---|---|
| 3,5-difluorobenzoyl chloride | 129714-97-2 |
| 3,5-dichlorobenzoyl chloride | 2905-62-6 |
| 3,5-dibromobenzoyl chloride | 23950-59-6 |
| 3,5-diethylbenzoyl chloride | 57664-62-7 |
| 3,5-dimethoxybenzoyl chloride | 17213-57-9 |
| 3,5-dimethylbenzoyl chloride | 6613-44-1 |
| 3,5-bis(trifluoromethyl)benzoyl chloride | 785-56-8 |
| 3-bromo-5-chlorobenzoyl chloride | 21900-27-6 |
| 3-chloro-5-methylbenzoyl chloride | 21900-22-1 |
| 3-methoxy-5-methylbenzoyl chloride | 96227-40-6 |
| 3-bromo-5-methoxybenzoyl chloride | 157893-14-6 |
| 3-chloro-5-methoxybenzoyl chloride | 89106-53-6 |
| 3-fluoro-5-(trifluoromethyl)benzoyl chloride | 171243-30-4 |
| 3,4,5-trimethoxybenzoyl chloride | 4521-61-3 |
| 3,4,5-trifluorobenzoyl chloride | 177787-26-7 |
| 3,4,5-trichlorobenzoyl chloride | 42221-50-1 |
| 3,4,5-trimethylbenzoyl chloride | 57498-46-1 |
| 4-bromo-3,5-dimethoxybenzoyl chloride | 56518-43-5 |
| 4-chloro-3,5-dimethoxybenzoyl chloride | 56518-47-9 |
| 3,5-dimethoxy-4-methylbenzoyl chloride | 34523-76-7 |
| 3,5-dibromo-4-methoxybenzoyl chloride | 4073-36-3 |
| 3,5-dichloro-4-methoxybenzoyl chloride | 29568-76-1 |
| 3,5-dichloro-4-methylbenzoyl chloride | 113485-46-4 |
| 3,5-dimethyl-4-methoxybenzoyl chloride | 21668-34-8 |
| 3,5-difluoro-4-methoxybenzoyl chloride | 501701-43-5 |
| 3,5-difluoro-4-methylbenzoyl chloride | 103877-74-3 |
| 3-bromo-4,5-dimethoxybenzoyl chloride | 70574-46-8 |
| 3,4-dichloro-5-methoxybenzoyl chloride | 63001-38-7 |
| 3,5-diethyl-4-methoxybenzoyl chloride | 59931-54-3 |
| 3,5-dibromo-4-fluorobenzoyl chloride | 402-85-7 |
| 2,3,5-trimethoxybenzoyl chloride | 119098-79-2 |
| 5-bromo-2,3-dimethoxybenzoyl chloride | 107188-91-0 |
| 3,5-dichloro-4-isopropoxybenzoyl chloride | 41490-23-7 |

-continued

| Benzoic acid | Cas No. |
|---|---|
| 3-chloro-4,5-dimethoxybenzoic acid | 20624-87-7 |
| 3,5-dimethoxy-4-isopropoxybenzoic acid | 52009-58-2 |
| 3,5-dihydroxy-4-methoxybenzoic acid | 4319-02-2 |
| 3,4-dihydroxy-5-methoxybenzoic acid | 3934-84-7 |
| 3-chloro-4-hydroxy-5-methoxybenzoic acid | 62936-23-6 |
| 3,5-dimethoxy-4-hydroxybenzoic acid | 329320-56-1 |
| 3,5-dichloro-4-hydroxybenzoic acid | 112290-09-2 |
| 3-bromo-5-chloro-4-hydroxybenzoic acid | 118276-15-6 |
| 3-bromo-4-hydroxy-5-methoxybenzoic acid | 6324-52-3 |
| 3-chloro-4-hydroxy-5-methylbenzoic acid | 35458-34-5 |

Appropriately substituted benzoic acids are known or may easily be synthesized by using standard procedures as known by those skilled in the art. It will be appreciated by those skilled in the art that in processes of the present invention certain functional groups such as hydroxyl groups in the starting reagents or intermediate compounds may need to be protected by protecting groups. Thus, the preparation of the compounds (I) may involve the addition and removal of one or more protecting groups. The protection and deprotection of functional groups is described in "Protective Groups in Organic Chemistry", edited by J. W. F. McOmie, Plenum Press (1973) and "Protective Groups in Organic Synthesis", $2^{nd}$ edition, T. W. Greene and P. G. M. Wuts, Wiley-Interscience (1991).

Suitable protecting groups for aromatic hydroxyl groups in the present invention are e.g. benzyl or isopropyl groups. Removal of the benzyl group and the isopropyl group is easily achieved by catalytic hydrogenation (catalyst Pd/carbon) and treatment with $BCl_3$, respectively.

The appropriately substituted acyl chlorides (X), where U=$CR_2$', V=N and W=CR6', can be synthesized under standard conditions from appropriately substituted isonicotinic acids with thionyl chloride. The appropriately substituted acyl chlorides (X), where U=N. V=$CR_4$' and W=$CR_6$' can be synthesized under standard conditions from 2-carboxylic acid substituted pyridines. The appropriately substituted acyl chlorides (X), where U=N, V=$CR_4$' and W=$CR_6$', or where U=$CR_2$', V=$CR_4$' and W=N; can be synthesized under standard conditions from appropriate 2-carboxylic acid substituted pyridines. The appropriately substituted acyl chorides (X), where U=$CR_2$' and V, W=N, can be synthesized under standard conditions from appropriate 4-carboxylic acid substituted pyrimidines. The appropriately substituted acyl chlorides (X), where U, W=N and V=$CR_4$' can be synthesized under standard conditions from appropriate substituted 2-carboxylic acid substituted pyrimidines. The appropriately substituted acyl chlorides (X), when U, V, W=N, can be substituted under standard conditions from appropriate 2-carboxylic acid substituted triazines.

Some examples of suitable starting materials for the production of nitrogen containing acid chlorides (X) are the following known compounds:

| | CAS No. |
|---|---|
| acid chloride (X) | |
| 4,6-dimethoxypyrimidine-2-carbonyl chloride | 509101-33-1 |
| Starting materials for production of (X) | |
| 2,6-dichloro-4-pyridinecarboxylic acid | 5398-44-7 |
| 2-chloro-6-methoxy-4-pyridinecarboxylic acid | 15855-06-84 |

-continued

| | CAS No. |
|---|---|
| 4,6-dichloro-2-pyridinecarboxylic acid | 88912-25-8 |
| 4,6-dimethoxy-2-pyridinecarboxylic acid | 90764-84-4 |
| 2,6-dichloro-4-pyrimidinecarboxylic acid | 16492-28-7 |
| 4,6-dichloro-1,3,5-triazine-2-carboxamide | 583630-76-6 |
| 4,6-dimethyl-1,3,5-triazine-2-ethylcarboxylate | 829-73-2 |
| 4,6-dimethoxy-1,3,5-triazine-2-carboxaldehyde | 98141-06-1 |

The transformation of amides, ethyl esters and aldehydes into their corresponding carboxylic acid derivatives are well-known reactions for those skilled in the art.

The compounds of the present invention contain a chiral center and therefore may exist in different enantiomeric forms. Although particularly preferred compounds (I) are enantiomerically pure the scope of the present invention is intended to cover both enantiomers per se, as well as mixtures of them in any ratio, such as racemic mixtures.

Compounds (I) of the present invention may be obtained in their enantiomerically pure forms by crystallization of their addition salts with chiral acids [see e.g. D. L. Minor et al. J. Med. Chem. 37 (1994) 4317-4328; U.S. Pat. No, 4,349,472], or alternatively, may be isolated by preparative HPLC using commercially available chiral phases. Other routes to the pure enantiomers of the products of the present invention are the use of asymmetric synthesis [M. J. Munchhof et al. J. Org. Chem. 60(1995) 7086-7087; R. P. Polniaszek et al. Tetrahedron Letters 28. (1987) 4511-4514], by asymmetric transfer hydrogenation of the intermediate imines (II) or iminium salts (III) [N. Uematsu et al. J. Am. Chem. Soc. 118 (1996) 4916-4917; G. Meuzelaar et al. Eur. J. Org. Chem. 1999, 2315-2321], or by resolution of chiral diastereometric derivatives thereof, as known by those skilled in the art.

The compounds of formula (I) and their pharmaceutically acceptable salts, where applicable, may be administered in the form of a pharmaceutical composition in which they are in association with a pharmaceutically acceptable adjuvant, diluent or carrier, in order to prevent or treat any disease in which inhibition of the IGF-1 receptor would be considered beneficial by the skilled person. The present invention also provides a pharmaceutical composition comprising a compound of formula (I), or a pharmaceutically acceptable salt thereof, as hereinbefore defined, in association with a pharmaceutically acceptable adjuvant, diluent or carrier. As to the appropriate excipients, diluents and adjuvants, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik und angrenzende Gebiete", by H. P. Fiedler, Editio Cantor, 2002 (in German).

The compounds (I) of the examples of the present invention have $IC_{50}$ activities in intact cell systems ranging from 8 microgram/ml to 150 picogram/ml. Due to the large difference in activities, the pharmaceutical compositions of the invention will preferably comprise from 0.001 to 50% by weight of compound (I).

The daily dose of compounds (I) will necessarily be varied depending upon the host treated, the particular route of administration, and the severity and kind of the illness being treated. Accordingly the optimum dosage may be determined by the practitioner who is treating any particular patient.

The pharmaceutical compositions of the invention may be formulated as creams, gels, solutions, ointments, suspensions or plasters etc. when intended for topical administration; for administration by inhalation, e.g. as aerosols or dry powders;

for oral administration, e.g. in the form of tablets, capsules, gels, syrups, suspensions, solutions, powders or granules; for rectal or vaginal administration e.g. as suppositories; or for parenteral injection (including intravenous, subcutaneous, intramuscular, intravascular, or infusion) as a sterile solution, suspension or emulsion.

The compounds of the present invention were found to down-regulate or inhibit the expression or function of the human IGF-1 receptor, without inhibiting the structurally closely related insulin receptor. They were found to promote apoptosis of malignant cells and to interfere with cell division by blocking the cells in the prophase of the mitotic cycle. The compounds (I) are useful for the prevention and/or treatment of diseases of unregulated IGF-1R expression, including cell proliferate diseases such as cancer, atherosclerosis, restenosis, inflammatory diseases e.g. psoriasis, autoimmune diseases e.g. rheumatoid arthritis, and transplant rejection. Some examples of cancers in which IGF-1R is unregulated or overexpressed and which can be prevented and/or treated by the compounds (I) of the invention include, but are not limited to, cancer of the breast, prostate, colon, lung, brain, pancreas, and melanoma, multiple myeloma, lymphoma and leukemia. Under the paragraph "Biological Data" are described some techniques to evaluate the sensitivity of cancer cells towards compounds (I) of the invention and the presence of the IGF-1 receptor.

Optionally the compounds (I) may be used against cell proliferate diseases in combination with conventional treatments such as irradiation and/or one or more chemotherapeutic agents such as e.g. Actinomycin, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplati, Pentostatin, Procarbazine, Streptozocin, Taxol, Temozolomide, Thiotepa, Tioguanine/Thioguanine, Topotecan, Treosulfan, Vinblastine, Vincristine, Vindesine or Vinoreline.

When a chemotherapeutic agent is used in combination with the compound of formula (I), then this may be used in the form of a medicament containing a combination of these two agents, for simultaneous administration, or they may be used in the form of separate dosage forms, each containing one of the agents, and in the latter case the individual dosage forms may be used e.g. sequentially, i.e. one dosage form with the compound (I), followed by a dosage form containing the chemotherapeutic agent (or vice versa). This embodiment of two separate dosage forms may be conceived and provided in the form of a kit.

In addition to their use in therapeutic medicine, the compounds (I) and their pharmaceutically acceptable salts are also useful as pharmacological tools in the development and standardization of in vitro and in vivo test systems for the evaluation of the effects of inhibitors of cell cycle activity in laboratory animals such as cats, dogs, rabbits, monkeys, rats and mice, as part of the search for new therapeutic agents.

EXAMPLES

Products described in the Examples have satisfactory proton nuclear magnetic resonance spectra and/or mass spectral data. Melting points are uncorrected. The substances described in the examples are racemates, unless marked with (−), which denotes the levorotatory enantiomer.

Examples 1 to 30

Syntheses of Racemic Compounds (I)

In the examples 1 to 30 the following general synthetic procedures were used:

1. Production of Amides (Scheme 2, IV):

The appropriate amine (VIII or IX, 0.1 mol) was added to an aqueous solution of sodium-hydroxide (200 ml, 2M) and dichloromethane (200 ml). To the vigorously stirred mixture containing the amine, the appropriate acyl chloride (X, 0.1 mol) dissolved in dichloromethane (200 ml) was added during 30 minutes at room temperature. After the addition, the mixture was stirred for further 60 minutes. The dichloromethane phase was separated, washed with hydrochloric acid (200 ml, 2M), dried (sodium sulphate) and concentrated to dryness. The residual amide (IV) is suitable without further purification as a starting material for the production of imines. All produced amides that were obtained in a crystalline state could be re-crystallized from methanol.

2. Production of Imines (Scheme 2, II):

A mixture of the appropriate amide (IV, 0.05-0.1 mol), toluene (200 ml) and phosphorus oxychloride (80 ml) was refluxed for 1.5-24 hours. The progress of the reaction was followed by TLC (silica gel/ethyl acetate or methanol). The reaction mixture was concentrated to dryness and partitioned between ethyl acetate (500 ml) and aqueous sodium hydroxide (400 ml, 2 M). The formed imine (II) was transferred into an aqueous phase by extraction of the organic phase with hydrochloric acid (3×200 ml, 2 M), which was made alkaline (pH 11-12) and extracted with dichloromethane. The organic phase was dried and concentrated to dryness giving the imine. If needed, most imines (II) could be purified by crystallization from diethyl ether or ethanol, or by crystallization of the corresponding hydrochlorides from ethanol.

3. Production of Secondary Amino Compounds (I) by Reduction of Imines (Schemes 1a and 1b):

A solution of the appropriate imine (II, 0.0 1-0.05 mol) in methanol (200 ml) was treated with an excess of sodium borohydride at room temperature until no starting material remained. The mixture was concentrated to dryness and partitioned between aqueous sodium hydroxide (300 ml, 2M) and dichloromethane (400 ml). The organic phase was separated, dried and concentrated to dryness leaving the pure secondary amine. The amino compound (I, $R_2$=hydrogen) could be crystallized from diethyl ether or ethanol, or by crystallization of the corresponding hydrochloride from ethanol or ethanol/diethyl ether.

4. Production of N-alkyl Compounds (Scheme 1a, III and I; $R_2$=Me or Et):

The appropriate imine (II, 0.005-0.01 mol) was dissolved in acetone (25-50 ml) and the selected alkyl halide MeX or EtX (1.2 equivalents) was added. The mixture was stirred at room temperature or at reflux temperature for 1-24 hours, depending upon the nature of the alkyl halide. After cooling to room temperature, the formed iminium salt (III) was filtered off and dried. The iminium salt so obtained was treated as described for the reduction of imines under paragraph 3 above. The compounds (I), with $R_2$=Me or Et, were crystallized from diethyl ether or ethanol, or by crystallization of the corresponding hydrochlorides from ethanol or ethanol/diethyl ether.

N-methyl compounds (I) could also be produced by Eschweiler-Clarke reaction. A mixture of the appropriate secondary amino compound (I, $R_2$=hydrogen, 0.005-0.01 mol), 1,2-dimethoxyethane (10 ml), formaldehyde (37% in water, 5 ml) and formic acid (5 ml) was heated at 80° C. for 5 hours. The reaction mixture was concentrated to dryness and the N-methyl compound (I) was isolated as described for secondary amino compounds (I) under paragraph 3.

5. Production of N-acetyl Compounds (Scheme 1b, I; $R_2$=COMe):

The appropriate secondary amino compound (I, 0.005-0.01 mol) was treated with acetic anhydride (150 ml) at room temperature during 24 hours. The mixture was concentrated to dryness leaving the N-acetyl compound (I), which was crystallized from methanol (except products from examples 6, 8, and 51 which were obtained as gums, and from examples 43, 44 and 47, which were isolated as amorphous solids).

6. Production of N-formyl Compounds (I, Schemes 1a and 1b):

A mixture of the appropriate secondary amino compound (I, 0.005-0.01 mol), formic acid (10 equivalents) and toluene (100 ml) was heated under reflux for 18 hours using a Dean-Stark trap. The reaction mixture was concentrated to dryness and the residue was dissolved in ethyl acetate. The organic phase was washed with 2M hydrochloric acid, dried and concentrated to dryness leaving the N-formyl compound (I).

7. Production of N-acyl Compounds (I, Schemes 1a and 1b):

A mixture of the appropriate secondary amino compound (I, 0.005-0.01 mol), pyridine (25 ml) and the selected acyl chloride $R_9$COCl (1.2 equivalents) was heated at 80° C. for two hours. The reaction mixture was concentrated to dryness and partitioned between ethyl acetate and 2M sodium hydroxide. The organic phase was washed with 2M hydrochloric acid, dried and concentrated to dryness, leaving the N-acyl compound (I).

8. Production of N-carboxylic Acid Ester Compounds (I, Schemes 1a and 1b):

A mixture of the appropriate secondary amino compound (I, 0.005-0.01 mol), anhydrous potassium carbonate (5 equivalents), acetone (100 ml) and the selected chloroformate $R_9$OCOCl (2 equivalents) was refluxed for 24 hours. The reaction mixture was concentrated to dryness, and the residue partitioned between hydrochloric acid (100 ml, 2 M) and dichloromethane (300 ml). The organic phase was dried and concentrated to dryness, giving the N-carboxylic acid ester compound (I).

9. Production of N-carboxylic Acid Amide Compounds I and N-carbothioic Acid Amide Compounds (I, Schemes 1a and 1b):

The appropriate secondary amino compound (I, 0.005-0.01 mol) was dissolved in acetonitrile (25 ml) and treated with the selected isocyanate $OCNR_9$ or isothiocyanate $SCNR_9$ (2 equivalents) at room temperature for 24 hours. The mixture was concentrated to dryness and the residue crystallized from methanol, giving the title compound (I).

10. Production of N-cyano Compounds (I, Schemes 1a and 1b):

A mixture of the appropriate secondary amino compound (I, 0.005-0.01 mol), 1,2-dimethoxyethane (10 ml), dry sodium carbonate (5 equivalents) and cyanogen halide, such as cyanogen bromide (2 equivalents) was heated at 50° C. for three hours. The reaction mixture was partitioned between dichloromethane (200 ml) and 2M hydrochloric acid (100 ml). The organic phase was dried and concentrated to dryness, leaving the N-cyano compound (I), which was crystallized from methanol.

By appropriate use of the above outlined general synthesis steps 1-10 racemic compounds (I) according to the following table 1 were prepared. Melting points given in the table are uncorrected.

TABLE 1

| Ex. | compound (I) | appearance | crystallization solvent | m.p. |
|---|---|---|---|---|
| 1 | 1-(3,5-dichlorophenyl)-2-acetyl-6-methoxy-1,2,3,4-tetrahydroisoquinoline | white solid | methanol | 134-137° C. |
| 2 | 1-(3,5-dibromophenyl)-2-acetyl-6-methoxy-1,2,3,4-tetrahydroisoquinoline | white solid | methanol | 170-173° C. |
| 3 | 1-(3,4,5-trimethoxyphenyl)-2-acetyl-6-methoxy-1,2,3,4-tetrahydroisoquinoline | white solid | methanol | 165-169° C. |
| 4 | 1-(3,5-dimethoxyphenyl)-2-acetyl-6-methoxy-1,2,3,4-tetrahydroisoquinoline | white solid | methanol | 152-154° C. |
| 5 | 1-(3,5-dimethylphenyl)-2-acetyl-6-methoxy-1,2,3,4-tetrahydroisoquinoline | white solid | ethanol | 120-122° C. |
| 6 | 1-[3,5-di(trifluoromethyl)Phenyl]-2-acetyl-6-methoxy-1,2,3,4-tetrahydroisoquinoline | viscous oil | — | — |
| 7 | 1-(2,6-dichloro-4-pyridyl)-2-acetyl-6-methoxy-1,2,3,4-tetrahydroisoquinoline | white solid | methanol | 163-166° C. |
| 8 | 1-(3,5-difluorophenyl)-2-acetyl-6-methoxy-1,2,3,4-tetrahydroisoquinoline | viscous oil | — | — |
| 9 | 1-(3,4,5-trimethoxyphenyl)-2-acetyl-6-ethoxy-1,2,3,4-tetrahydroisoquinoline | white solid | methanol | 138-140° C. |
| 10 | 1-(3,4,5-trimethoxyphenyl)-2-acetyl-5,6-dimethoxy-1,2,3,4-tetrahydroisoquinoline | white solid | methanol | 166-168° C. |
| 11 | 1-(3,4,5-trimethoxyphenyl)-2-acetyl-6-methyl-1,2,3,4-tetrahydroisoquinoline | white solid | methanol | 176-178° C. |
| 12 | 1-(3,4,5-trimethoxyphenyl)-2-formyl-6-methoxy-1,2,3,4-tetrahydroisoquinoline | white solid | methanol | 103-105° C. |
| 13 | 1-(3,4,5-trimethoxyphenyl)-2-methyl-6-methoxy-1,2,3,4-tetrahydroisoquinoline | white solid | methanol | 94-95° C. |
| 14 | 1-(3,4,5-trimethoxyphenyl)-6-methoxy-1,2,3,4-tetrahydroisoquinoline | white solid | acetone | 118-120° C. |
| 15 | 1-(3,5-dichlorophenyl)-2-methyl-6-methoxy-1,2,3,4-tetrahydroisoquinoline | white solid | diethyl ether | 112-115° C. |
| 16 | 1-(3,5-dichlorophenyl)-2-ethyl-6-methoxy-1,2,3,4-tetrahydroisoquinoline hydrochloride | white solid | ethanol/diethyl ether | 195-199° C. |
| 17 | 1-(3,5-dimethoxyphenyl)-6-methoxy-1,2,3,4-tetrahydroisoquinoline-2-carbothioic acid ethyl amide | white solid | methanol | 149-151° C. |

TABLE 1-continued

| Ex. | compound (I) | appearance | crystallization solvent | m.p. |
|---|---|---|---|---|
| 18 | 1-(3,5-dimethoxyphenyl)-6-methoxy-1,2,3,4-tetrahydroisoquinoline-2-carboxylic acid ethyl amide | white solid | methanol | 142-144° C. |
| 19 | 1-(3,5-dimethoxyphenyl)-6-methoxy-1,2,3,4-tetrahydroisoquinoline-2-carboxylic acid methyl ester | white solid | methanol | 87-89° C. |
| 20 | 1-(3,4,5-trimethoxyphenyl)-2-acetyl-6-isopropoxy-1,2,3,4-tetrahydroisoquinoline | white solid | methanol | 109-111° C. |
| 21 | 1-(3,5-dichlorophenyl)-6-methoxy-1,2,3,4-tetrahydroisoquinoline | white solid | diethyl ether | 122-124° C. |
| 22 | 1-(2,3-dimethoxy-5-bromophenyl)-2-acetyl-6-methoxy-1,2,3,4-tetrahydroisoquinoline | pale yellow amorphous solid | — | — |
| 23 | 1-(3,4,5-trimethoxyphenyl)-2-cyano-6-ethoxy-1,2,3,4-tetrahydroisoquinoline | white solid | methanol | 137-139° C. |
| 24 | 1-(3-chloro-4,5-dimethoxyphenyl)-2-acetyl-6-methoxy-1,2,3,4-tetrahydroisoquinoline | white solid | methanol | 173-175° C. |
| 25 | 1-(3-chloro-4-isopropoxy-5-methoxy)-2-acetyl-6-methoxy-1,2,3,4-tetrahydroisoquinoline | White solid | methanol | 117-119° C. |
| 26 | 1-(3-chloro-4-hydroxy-5-methoxy)-2-acetyl-6-methoxy-1,2,3,4-tetrahydroisoquinoline | White solid | methanol | 189-191° C. |
| 27 | 1-(2,6-dichloro-4-pyridyl)-2-formyl-6-methoxy-1,2,3,4-tetrahydroisoquinoline | white solid | methanol | 138-140° C. |
| 28 | 1-(3-chloro-4-acetyloxyoxy-5-methoxy)-2-acetyl-6-methoxy-1,2,3,4-tetrahydroisoquinoline | white solid | ethanol | 205-215° C. (dec) |
| 29 | 1-(3-chloro-4-cyclopentyloxy-5-methoxy)-2-acetyl-6-methoxy-1,2,3,4-tetrahydroisoquinoline | white solid | ethanol | 228-232° C. |
| 30 | 1-(3,5-dichlorophenyl)-2-methyl-7-methoxy-2,3,4,5-tetrahydro-1H-2-benzazepine | white solid | diethyl ether | 121-123° C. |
| 31 | 1-(3,4,5-trimethoxyphenyl)-2-methyl-7-methoxy-2,3,4,5-tetrahydro-1H-2-bezazepine hydrochloride | White solid | diethyl ether | 165-167° C. |
| 32 | 1-(3,4,5-trimethoxyphenyl)-7-methoxy-2,3,4,5-tetrahydro-1H-2-benzazepine | White solid | diethyl ether | 127-129° C. |

Examples 33-40

Syntheses of Enantiomerically Pure Compounds (I)

Example 33

(−)-1-(3,4,5-trimethoxyphenyl)-2-cyano-6-methoxy-1,2,3,4-tetrahydroisoquinoline 1. 3-Methoxyphenylethylamine (25.0 g) was added to an aqueous solution of sodium hydroxide (200 ml, 2M) and dichloromethane (200 ml). To the vigorously stirred mixture containing the amine, 3,4,5-trimethoxybenzoyl chloride (38.1 g) dissolved in dichloromethane (200 ml) was added during 30 minutes at room temperature. After the addition, the mixture was stirred for further 60 minutes. The dichloromethane phase was separated, washed with hydrochloric acid (200 ml, 2M), dried (sodium sulphate) and concentrated to dryness. The residual amide (57.2 g) is suitable without further purification as a starting material for the production of the corresponding imine. An analytical sample was obtained by crystallization from methanol, giving a white solid, m.p. 115-117° C.

2. A mixture of the amide from step 1 (52.0 g), toluene (350 ml) and phosphorus oxychloride (140 ml) was heated under reflux for 1.5 hours. The reaction mixture was concentrated to dryness and partitioned between ethyl acetate (500 ml) and aqueous sodium hydroxide (400 ml, 2 M). The formed imine was transferred into an aqueous phase by extraction of the organic phase with hydrochloric acid (3×300 ml, 2 M), which was made alkaline (pH 11-12) and extracted with dichloromethane. The organic phase was dried and concentrated to dryness giving the imine, (48.2 g). An analytical sample was obtained by crystallization from methanol giving a white solid, m.p. 141-143° C.

3. The imine produced according to step 2 (69.3 g) was dissolved in a mixture of methanol (500 ml) and 1,2-dimethoxyethane (300 ml) and treated with sodium borohydride at room temperature until no starting material remained (TLC: silica gel/methanol). The mixture was concentrated to dryness and partitioned between aqueous sodium hydroxide (500 ml, 2M) and dichloromethane (500 ml). The organic phase was separated, dried and concentrated to dryness, leaving the secondary amine (67.8 g). An analytical sample was obtained by crystallization from ethyl acetate, giving a white solid, m.p. 118-120° C.

4. The secondary amine (48.3 g) produced according to is step 3 was dissolved in hot ethanol (600 ml) and the solution was added to acetyl-D-leucine (25.0 g) dissolved in hot ethanol (200 ml). The mixture was allowed to reach room temperature during 24 hours, after which it was filtered. The retained crystals were washed with ethanol (200 ml) and dried giving a white solid (60.0 g, 10.9% ee). A second crystallization (59.7 g) from ethanol (1400 ml) gave a white solid (39.2 g, 37.9% ee). A third crystallization (39.0 g ) from ethanol (1150 ml) gave a white solid (26.0 g, 77.2% ee). A fourth crystallization (25.7 g) from ethanol (900 ml) gave a white solid (21.6 g, 99.9% ee). The product from the last crystallization was partioned between dichloromethane (400 ml) and aqueous sodium hydroxide.(400 ml, 2M). The organic phase was dried and concentrated to dryness, leaving the (−) enantiomer (13.9 g). Crystallization from ethanol gave the pure (−) enantiomer (12.4 g, 100.0% ee). The corresponding hydrochloride, crystallized from methanol, was used for characterization purposes, m.p. 270-275° C. (dec.), $[\alpha]_D^{20}$ −46.8° (c=0.051, DMF).

5. A mixture of the pure enantiomer (0.50 g) from step 4,1,2-dimethoxyethane (20 ml), dry sodium carbonate (0.30 g) and cyanogen bromide (0.35 g) was heated at 50 EC for three hours. The reaction mixture was partioned between dichloromethane (200 ml) and hydrochloric acid (100 ml, 2M). The organic phase was dried and concentrated to dryness. The residue was crystallized from methanol giving the title compound as a white solid (0.36 g), m.p.132-134° C., $[\alpha]_D^{20}$ −93.2° (c=1.0, $CHCl_3$)

Example 34

(−)-1-(3,5-dichlorophenyl)-2-acetyl-6-methoxy-1,2,3,4-tetrahydroisoquinoline 1. 3-Methoxyphenylethylamine (18.1 g) was added to an aqueous solution of sodium hydroxide (200 ml, 2M) and dichloromethane (200 ml). To the vigorously stirred mixture containing the amine, 3,5-dichlorobenzoyl chloride (25.0 g) dissolved in dichloromethane (200 ml) was added during 30 minutes at room temperature. After the addition, the mixture was stirred for further 60 minutes. The dichloromethane phase was separated, washed with hydrochloric acid (200 ml, 2M), dried (sodium sulphate) and concentrated to dryness. The residual amide (40.6 g) is suitable without further purification as a starting material for the production of the corresponding imine. An analytical sample was obtained by crystallization from methanol, giving a white solid, m.p. 111-113° C.

2. A mixture of the amide from step 1 (35.8 g), toluene (200 ml) and phosphorus oxychloride (80 ml) was heated under reflux for 6 hours. The reaction mixture was concentrated to dryness and partitioned between ethyl acetate (500 ml) and aqueous sodium hydroxide (400 ml, 2 M). The ethyl acetate phase was dried and concentrated to dryness. The residue was crystallized from methanol, giving the imine (24.0 g), m.p. 110-113° C.

3. The imine from step 2 (18.2 g.) was dissolved in methanol (300 ml) containing 1.05 equivalents of acetic acid and treated with an excess of sodium cyanoborohydride at room temperature until no starting material remained (TLC: silica gel-ethyl acetate). The mixture was concentrated to dryness and partitioned between aqueous sodium hydroxide (300 ml, 2M) and dichloromethane (400 ml). The organic phase was separated, dried and concentrated to dryness leaving the secondary amine (17.7 g). An analytical sample was obtained by crystallization from ethanol, m.p. 122-124° C.

4. The secondary amine (46.0 g) produced according to step 3 was dissolved in hot ethanol (800 ml) and the solution was added to N-acetyl-D-leucine (25.84 g) dissolved in hot ethanol (650 ml). The mixture was allowed to reach room temperature during the night, after which it was filtered. The retained crystals were washed with ethanol (150 ml) and thereafter partioned between dichloromethane (500 ml) and aqueous sodium hydroxide (400 ml, 2M). The organic phase was dried and concentrated to dryness, leaving the levorotatory enantiomer (6.9 g, 99.3% ee). Crystallization from ethanol gave the pure (−)-enantiomer (5.2 g), m.p. 94-95° C., $[\alpha]_D^{20}$ −24.8° (c=1.5, $CHCl_3$).

5. The (−)-enantiomer from step 4 (1.6 g) was treated with acetic anhydride (100 ml) at room temperature during 24 hours. The mixture was concentrated to dryness and the residue was partioned between dichloromethane (200 ml) and hydrochloric acid (2M, 100 ml). The organic phase was dried and concentrated to dryness, leaving the title compound as a white amorphous solid, $[\alpha]_D^{20}$ −154.9° (c=1.52, $CHCl_3$)

Example 35

(−)-1-(2,6-dichloro-4-pyridyl)-2-formyl-6-methoxy-1,2,3,4-tetrahydroisoquinoline 1. A mixture of 2,6-dichloroisonicotinic acid (26.1 g), thionyl chloride (140 ml) and 1,2-dimethoxyethane (70 ml) was refluxed for 6 hours. The excess of thionyl chloride and solvent were evaporated leaving the acid chloride.

3-Methoxyphenylethylamine (20.6 g) was added to an aqueous solution of sodium hydroxide (300 ml, 2M) and dichloromethane (400 ml). To the vigorously stirred mixture containing the amine, the acid chloride from above, dissolved in 1,2-dimethoxyethane (50 ml), was added during 30 minutes at room temperature. After the addition, the mixture was stirred for further 60 minutes. The dichloromethane phase was separated, dried and concentrated to dryness. The residual amide was crystallized from methanol, giving a white solid (31.6 g), m.p. 105-108° C.

2. A mixture of the amide produced according to step 1 (38.0 g), toluene (300 ml) and phosphorus oxychloride (80 ml) was heated under reflux for 5 hours. The reaction mixture was concentrated to dryness and partitioned between ethyl acetate (500 ml) and aqueous sodium hydroxide (400 ml, 2 M). The formed imine was transferred into an aqueous phase by extraction of the organic phase with hydrochloric acid (5×300 ml, 2 M), which was made alkaline (pH 11-12) and extracted with dichloromethane. The organic phase was dried and concentrated to dryness giving the crude imine (27.3 g). Crystallization from methanol gave the imine (22.8 g). An analytical sample was obtained by re-crystallization from acetone, giving a white solid, m.p. 130-133° C.

3. A mixture of benzeneruthenium(II) chloride dimer (19 mg), (−)-(1S,2S)-N-(naphthalene-1-sulfonyl)-1,2-diphenyl-ethylenediamine (31 mg) [G. J. Meuzelaar et al. Eur.J.Org.Chem.(1999) 2315-2321], triethylamine (0.5 ml) and acetonitrile was heated with stirring under nitrogen at 80° C. for one hour. After cooling to room temperature, the imine from step 2 (4.0 g) dissolved in acetonitrile (10 ml) and an azeotropic mixture of formic acid and triethylamine (10 ml, 5:2) were added to the mixture containing the catalyst. After 20 hours of reaction, the same amount of catalyst and azeotropic mixture were added to the reaction mixture. After a total reaction time of 47 hours, the reaction mixture was partioned between aqueous sodium hydroxide (250 ml, 1M) and ethyl acetate. The organic phase was dried and concentrated to dryness. The residue was purified by chromatography on silica gel (40-63 μM, 6×21 cm) using ethyl acetate as eluent. The fraction containing the secondary amine was concentrated to dryness. The residual amine was transferred into its hydrochloric salt by treatment with hydrogen chloride in methanol (1.25 M, 15 ml). Crystallization from methanol afforded the amine hydrochloride (0.72 g, 99.8% ee), m.p. 221-260° C. (dec.), $[\alpha]_D^{20}$ −28.90 (c=0.72, DMF).

4. A mixture of the free amine from step 3 (0.60 g), formic acid (2 ml) and toluene (100 ml) was heated under reflux for 18 hours using a Dean-Stark trap. The reaction mixture was concentrated to dryness and the residue was dissolved in ethyl acetate (200 ml), which was washed with aqueous sodium hydroxide (100 ml, 2M), dried and concentrated to dryness leaving the formyl derivative as a solid. Crystallization from methanol gave the title compound as a white solid (0.52 g, 100.0% ee), m.p. 156-158° C, $[\alpha]_D^{20}$ −213.1° (c=1.05, CHCl$_3$).

Examples 36-40

Syntheses of Additionally Five Enantiomerically Pure Compounds (I)

The enantiomeric pure compounds 34, 36 and 37 were synthesized from the enantiomerically pure secondary amine described in Example 32, step 4, by using the using the above outlined general synthesis steps 4-10. Compound 38 was synthesized from the enantiomerically pure secondary amine described in Example 31, step 4, by using the general synthesis step 6. Compound 35 was synthesized by reduction of 1-(3,5-dimethoxyphenyl)-6-methoxy-3,4-dihydroisoquinoline by asymmetric transfer hydrogenation in accordance with Example 33, step 3, followed by crystallization of the hydrochloride of the formed secondary amine from ethanol. The enantiomerically pure secondary amine was transferred into its formyl derivative by applying step 6 of the general synthesis description. The properties of compounds 36-40 are described in the following Table 2:

TABLE 2

| | | | |
|---|---|---|---|
| 36 (−)-1-(3,5-dichlorophenyl)-2-formyl-6-methoxy-1,2,3,4-tetrahydroisoquinoline $[\alpha]_D^{20}$ = −206.7° (c = 1.01, CHCl$_3$) | white amorphous solid | — | — |
| 37 (−)-1-(3,5-dimethoxyphenyl)-2-formyl-6-methoxy-1,2,3,4-tetrahydroisoquinoline $[\alpha]_D^{20}$ = −223.2° (c = 1.04, CHCl$_3$) | white solid | diethyl ether | 86-88° C. |
| 38 (−)-1-(3,5-dichlorophenyl)-2-methyl-6-methoxy-1,2,3,4-tetrahydroisoquinoline $[\alpha]_D^{20}$ = −138.3° (c = 1.49, CHCl$_3$) | white solid | diethyl ether | 101-103° C. |
| 39 (−)-1-(3,5-dichlorophenyl)-2-cyano-6-methoxy-1,2,3,4-tetrahydroisoquinoline $[\alpha]_D^{20}$ = −101.6° (c = 0.74, CHCl$_3$). | yellowish amorphous solid | — | — |
| 40 (−)-1-(3,4,5-trimethoxyphenyl)-2-acetyl-6-methoxy-1,2,3,4-tetrahydroisoquinoline $[\alpha]_D^{20}$ = −190.8° (c = 1.02, CHCl$_3$) | white solid | methanol | 119-123° C. |

Biological Data

Cell Growth Inhibition Study on Human Cancer Cell Lines Jurkat, MCF-7 and SK-MEL 28

MCF-7 and SK-MEL 28 cells (~5000 cells/100 μl) were transferred into 96 well plates and grown, with or without the test compounds, for 48 hours at 37° C. in RPMI medium (Gibco) supplemented with 10% fetal calf serum containing penicillin and streptomycin (Gibco). The same procedure was followed for Jurkat cells, except for the density of cells (~50000 cells/100 μl) and that the incubation time was limited to 24 hours. At the end of the incubation times, the cell growth inhibition of the Jurkat and SK-MEL 28 cell lines were determined by the use of CellTiter 96 (Promega) and MCF-7 with a methylene blue test. The compounds of the examples were found to have in the above tests an IC$_{50}$ of from 8 microgram/ml to 150 picogram/ml in at least one cell line.

Cell Death by Apoptosis

Jurkat and SK-MEL 28 cells were incubated with the compound (I) from example 3 for 6, 24 and 48 hours, after which the percentage of apoptotic cells were determined by Annexin V staining. The results are depicted in the Table 3 below.

TABLE 3

| | Jurkat | | SK-Mel-28 | | |
|---|---|---|---|---|---|
| | 6 hours | 24 hours | 6 hours | 24 hours | 48 hours |
| vehicle | 8 | 9 | 12 | 8 | 9 |
| compound 3, 500 ng/ml | 8 | 89 | 8 | 16 | 70 |
| SuperFasL, 1000 ng/ml | 48 | 84 | 8 | 22 | 27 |

The numbers depicted in the Table represent the percentage of Annexin-V positive cells.

From the results in Table 3 above it is obvious that the compound from example 3 induces apoptosis in the tested cell lines, but with a slower kinetics than SuperFasL.

Interaction with Cell Division

The mitotic index was determined after incubation of SK-Mel-28 cells with vehicle, the compound (I) of example 3 and nocodazole for four hours [essentially as described by C. L. Rieder et al.: Current Biology 10(2000) 1067-1070]. The results are given in table 4 below.

TABLE 4

| | mitotic index SK-Mel-28 |
|---|---|
| vehicle | 1.7 |
| compound of example 3, 300 ng/ml | 5 |
| Nocodazole, 10 μM | 2.9 |

The tested substances block the cells in the prophase stage of mitosis.

Inhibition of Phosphorylation of IGF-1R and Insulin Receptor (IR) in SK-MEL-28

IGF-1R: Assay without treatment with compounds (I). (Essentially as described by M. Rubini et al. Exp. Cell Res. 230(1997) 284-292).

SK-MEL-28 cells (density 60000/cm$^2$; 100 mm diameter dish containing 10 ml RPMI 1640) were starved for 24 hours at 37° C. and thereafter treated for 5 minutes at 37° C. with IGF-1 (200 ng, Sigma). Untreated cells served as control. The cells were lyzed and subjected to immunoprecipitation using a specific antibody against IGF-1R (alfa-IR3, Oncogene Science). Immunoprecipitates were separated by polyacrylamide gel electrophoresis and transferred to nitrocellulose membranes (Amersham Bioscience). The immunoprecipitated IGF-1 receptor was located on the nitrocellulose membrane using an antibody against the alfa-subunit of the IGF-1R (N-20:sc-712, Santa Cruz Biotech.). Detection of the tyrosine phosphorylation of the IGF-1 receptor was performed by incubation of the nitrocellulose membranes with an anti-phosphotyrosine antibody (4G10, Upstate Biotechnology Ltd., UK). To reveal the anti-IGF-1R rabbit polyclonal antibody and the anti-phosphotyrosine mouse monoclonal antibody, the membranes were incubated with anti-rabbit IgG and anti-mouse IgG antibodies coupled to HRP, respectively, and visualized by the use of an enhanced chemiluminescence (ECL) detection system (Pierce).

IGF-1R: Assay with Treatment with Compounds (I).

Starved SK-MEL-28 cells (60000 cells./cm$^2$; 100 mm diameter dish; containing 10 ml RPMI 1640) were treated for 2 hours with 10 microgram of compound 31. After 2 hours of treatment., the cells were stimulated for 5 minutes at 37° C. with 200 ng of IGF-1, and thereafter treated as described above.

TABLE 5

Percentage of IGF-1R phosphorylation in SK-MEL-28 cells.

| Compound 31 | 0 ng/ml | 0 ng/ml | 1000 ng/ml |
|---|---|---|---|
| IGF-1 | 0 ng/ml | 20 ng/ml | 20 ng/ml |
| % phosphorylation | 0 | 100 | 10 |

IR: Assay with and without Treatment with Compounds (I).

SK-MEL-28 cells (density 60000/cm$^2$) were grown in 100 mm diameter dishes containing 10 ml RPMI 1640 supplemented with 10% fetal bovine serum (FBS) for 24 hours. After 24 hours fresh medium supplemented with 10% FBS was added together with or without 1 microgram/ml of compound 33. The dishes were incubated at 37° C. for 2 hours, after which the cells were lyzed and subjected to immunoprecipitation using 2 microliter of an anti-IR monoclonal antibody (18-44, ABCAM) and 20 microliter of agarose-conjugated protein G. Antibody-antigen complexes were allowed to form for 4 hours at 4° C. and after that collected by centrifugation at 4° C. for 1 minute at 5000 rpm. Immunoprecipitated complexes were separated by electrophoresis on an 8% polyacrylamide gel and electroblotted onto a nitrocellulose membrane (Amersham Bioscience). The efficiency of the immunoprecipitation was determined by using a polyclonal antibody against the beta-subunit of the insulin receptor (C-19; Santa Cruz Biotech.). Detection of the tyrosine phosphorylation of the insulin receptor was performed by incubation of the nitrocellulose membranes with an anti-phosphotyrosine antibody (4G10, Upstate Biotechnology Ltd., UK). To reveal the anti-IR rabbit polyclonal antibody and the anti-phosphotyrosine mouse monoclonal antibody, the membranes were incubated with anti-rabbit IgG and anti-mouse IgG anti-bodies coupled to HRP, respectively, and visualized by the use of an enhanced chemiluminescence (ECL) detection system (Pierce).

No difference in phosphorylation of the insulin receptor was detected between untreated cells and cells treated with 1 microgram/ml of compound 33.

The invention claimed is:
1. A compound of the following formula (I):

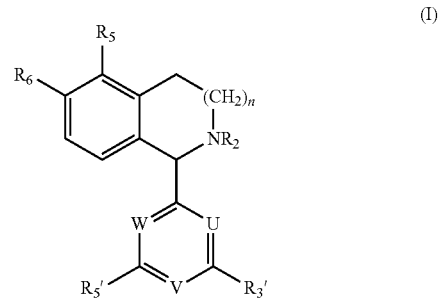

wherein
$R_2$ designates hydrogen, Me, Et, CHO, CN, OH, OMe, COR$_9$, COOR$_9$, CONHR$_9$ or CSNHR$_9$, whereby R$_9$ denotes (C$_1$-C$_4$) alkyl;
$R_5$ designates hydrogen, (C$_1$-C$_4$) alkyl , OH, (C$_1$-C$_4$) alkoxy, OCF$_3$, trifluoromethyl or halogen;
$R_6$ designates Me, (C$_1$-C$_4$) alkoxy, OCF$_3$, SMe or SEt;
n is 1 or 2;
$R_3'$ and $R_5'$ each independently designate OH, Me, Et, OMe, OCF$_3$, trifluoromethyl or halogen;
U designates N or CR$_2'$, whereby R$_2'$ denotes hydrogen, (C$_1$-C$_4$) alkyl, (C$_1$-C$_4$) alkoxy, trifluoromethyl or halogen;
V designates N or CR$_4'$, whereby R$_4'$ denotes hydrogen, (C$_1$-C$_6$) alkoxy, (C$_1$-C$_6$) alkyl, OH, trifluoromethyl or halogen;
W designates N or CR$_6'$, whereby R$_6'$ denotes hydrogen, (C$_1$-C$_4$) alkyl, (C$_1$-C$_4$) alkoxy, trifluoromethyl or halogen; or pharmaceutically acceptable salt thereof.

2. A compound according to claim 1, wherein R$_2$ designates Me, OH, CN, CHO, COR$_9$ or COOR$_9$.

3. A compound according to claim 1, wherein R$_2$ designates Me, CN, CHO or COMe.

4. A compound according to claim 1, wherein R$_5$ designates hydrogen, Me, OMe or halogen.

5. A compound according to claim 1, wherein R$_6$ designates OMe or OEt.

6. A compound according to claim 1, wherein R$_5$ designates hydrogen or OMe; and R$_6$ designates OMe.

7. A compound according to claim 1, wherein R$_3'$ and R$_5'$ each independently designate chloro, bromo, Me or OMe.

8. A compound according to claim 1, wherein R$_3'$ and R$_5'$ are identical; or R$_3'$ designates chloro or bromo, and R$_5'$ designates OMe.

9. A compound according to claim 7, wherein R$_3'$ and R$_5'$ designate both chloro or both bromo.

10. A compound according to claim 1, wherein U and W designate CH and V designates CR$_4'$.

11. A compound according to claim 10, wherein R$_4'$ designates hydrogen, chloro, bromo, Me or OMe.

12. A compound according to claim 10, wherein R$_3'$, R$_4'$ and R$_5'$ designate OMe; or R$_3'$ designates chloro and R$_4'$ and R$_5'$ designate OMe; or R4' designates hydrogen and R$_3'$ and R$_5'$ designate both chloro or both bromo.

13. The compound according to claim 1, wherein the compound is one selected from the group consisting of 1-(3,5-dichlorophenyl)-2-formyl-6-methoxy-1,2,3,4-tetrahydroisoquinoline, 1-(3,5-dichlorophenyl)-2-acetyl-6-methoxy-1,2,3,4-tetrahydroisoquinoline, 1-(3,5-dichlorophenyl)-2-cyano-6-methoxy-1,2,3,4-tetrahydroisoquinoline, 1-(3,5- dibromophenyl)-2-formyl-6-methoxy-1,2,3,4-tetrahydroisoquinoline, 1-(3,5-dibromophenyl)-2-acetyl-6-methoxy-1,2,3,4-tetrahydroisoquinoline, 1-(3,5-dibromophenyl)-2-cyano-6-methoxy-1,2,3,4-tetrahydroisoquinoline, 1-(3,5-dimethoxyphenyl)-2-formyl-6-methoxy-1,2,3,4-tetrahydroisoquinoline, 1-(3,5-dimethoxyphenyl)-2-acetyl-6-methoxy-1,2,3,4-tetrahydroisoquinoline, 1-(3,5-dimethoxyphenyl)-2-cyano-6-methoxy-1,2,3,4-tetrahydroisoquinoline, 1-(3,4,5-trimethoxyphenyl)-2-formyl-6-methoxy-1,2,3,4-tetrahydroisoquinoline, 1-(3,4,5-trimethoxyphenyl)-2-acetyl-6-methoxy-1,2,3,4-tetrahydroisoquinoline, 1-(3,4,5-trimethoxyphenyl)-2-cyano-6-methoxy-1,2,3,4-tetrahydroisoquinoline, 1-(3-chloro-4,5-dimethoxyphenyl)-2-formyl-6-methoxy-1,2,3,4-tetrahydroisoquinoline, 1-(3-chloro-4,5-dimethoxyphenyl)-2-acetyl-6-methoxy-1,2,3,4-tetrahydroisoquinoline 1-(3-chloro-4,5-dimethoxyphenyl)-2-cyano-6-methoxy-1,2,3,4-tetrahydroisoquinoline, 1-(3,5-dichlorophenyl)-2-formyl-6-ethoxy-1,2,3,4-tetrahydroisoquinoline, 1-(3,5-dichlorophenyl)-2-acetyl-6-ethoxy-1,2,3,4-tetrahydroisoquinoline, 1-(3,5-dichlorophenyl)-2-cyano-6-ethoxy-1,2,3,4-tetrahydroisoquinoline, 1-(3,5-dibromophenyl)-2-formyl-6-ethoxy-1,2,3,4-tetrahydroisoquinoline, 1-(3,5-dibromophenyl)-2-acetyl-6-ethoxy-1,2,3,4-tetrahydroisoquinoline, 1-(3,5-dibromophenyl)-2-cyano-6-ethoxy-1,2,3,4-tetrahydroisoquinoline, 1-(3,5-dimethoxyphenyl)-2-formyl-6-ethoxy-1,2,3,4-tetrahydroisoquinoline, 1-(3,5-dimethoxyphenyl)-2-acetyl-6-ethoxy-1,2,3,4-tetrahydroisoquinoline, 1-(3,5-dimethoxyphenyl)-2-cyano-6-ethoxy-1,2,3,4-tetrahydroisoquinoline, 1-(3,4,5-trimethoxyphenyl)-2-formyl-6-ethoxy-1,2,3,4-tetrahydroisoquinoline, 1-(3,4,5-trimethoxyphenyl)-2-acetyl-6-ethoxy-1,2,3,4-tetrahydroisoquinoline, 1-(3,4,5-trimethoxyphenyl)-2-cyano-6-ethoxy-1,2,3,4-tetrahydroisoquinoline, 1-(3-chloro-4,5-dimethoxyphenyl)-2-formyl-6-ethoxy-1,2,3,4-tetrahydroisoquinoline, 1-(3-chloro-4,5-dimethoxyphenyl)-2-acetyl-6-ethoxy-1,2,3,4-tetrahydroisoquinoline or 1-(3-chloro-4,5-dimethoxyphenyl)-2-cyano-6-ethoxy-1,2,3,4-tetrahydroisoquinoline, 1-(3,5-dichlorophenyl)-2-formyl-5,6-dimethoxy-1,2,3,4-tetrahydroisoquinoline, 1-(3,5-dichlorophenyl)-2-acetyl-5,6-dimethoxy-1,2,3,4-tetrahydroisoquinoline, 1-(3,5-dichlorophenyl)-2-cyano-5,6-dimethoxy-1,2,3,4-tetrahydroisoquinoline, 1-(3,5-dibromophenyl)-2-formyl-5,6-dimethoxy-1,2,3,4-tetrahydroisoquinoline, 1-(3,5-dibromophenyl)-2-acetyl-5,6-dimethoxy-1,2,3,4-tetrahydroisoquinoline, 1-(3,5-dibromophenyl)-2-cyano-5,6-dimethoxy-1,2,3,4-tetrahydroisoquinoline, 1-(3,5-dimethoxyphenyl)-2-formyl-5,6-dimethoxy-1,2,3,4-tetrahydroisoquinoline, 1-(3,5-dimethoxyphenyl)-2-acetyl-5,6-dimethoxy-1,2,3,4-tetrahydroisoquinoline, 1-(3,5-dimethoxyphenyl)-2-cyano-5,6-dimethoxy-1,2,3,4-tetrahydroisoquinoline, 1-(3,4,5-trimethoxyphenyl)-2-formyl-5,6-dimethoxy-1,2,3,4-tetrahydroisoquinoline, 1-(3,4,5-trimethoxyphenyl)-2-acetyl-5,6-dimethoxy-1,2,3,4-tetrahydroisoquinoline, 1-(3,4,5-trimethoxyphenyl)-2-cyano-5,6-dimethoxy-1,2,3,4-tetrahydroisoquinoline 1-(3-chloro-4,5-dimethoxyphenyl)-2-formyl-5,6-dimethoxy-1,2,3,4-tetrahydroisoquinoline, 1-(3-chloro-4,5-dimethoxyphenyl)-2-acetyl-5,6-dimethoxy-1,2,3,4-tetrahydroisoquinoline or 1-(3-chloro-4,5-dimethoxyphenyl)-2-cyano-5,6-dimethoxy-1,2,3,4-tetrahydroisoquinoline, and pharmaceutically acceptable salts thereof.

14. A compound according to claim 1, which is the (R)- or (S)-enantiomer.

15. A medicament, comprising the compound according to claim 1.

16. A pharmaceutical composition, comprising: the compound of formula (I), or the pharmaceutically acceptable salt thereof according to claim 1; and a pharmaceutically acceptable adjuvant, diluent or carrier.

17. A kit, comprising:
the compound of the formula (I) or the pharmaceutically acceptable salt thereof according to claim 1, and a chemotherapeutic agent, as a combination for the simultaneous, separate or successive administration in the therapy of a disease in which down-regulation or inhibition of the expression or function of the IGF-1 receptor is beneficial.

18. A method of evaluating the effects of inhibitors interfering with cell division by blocking cells in prophase of the mitotic cycle, comprising utilizing the compound according to claim 1 as a pharmacological tool in the development and standardization of in vitro and in vivo test systems for the cells.

19. A method of treatment of leukemia, breast cancer, melanoma cancer or prostate cancer in which down-regulation or inhibition of the expression or function of the IGF-1 receptor is beneficial, in a subject in need of such treatment, comprising administering to said subject an amount of the compound of formula (I) according to claim 1 in an amount which is effective in down-regulating or inhibiting the expression or function of the IGF-1 receptor.

20. A method of preparing a medicament for the prophylaxis or treatment of a disease in which down-regulation or inhibition of the expression or function of the IGF-1 receptor is beneficial, comprising utilizing the compound according to claim 1.

21. The method according to claim 20, wherein the disease is selected from cell proliferate diseases selected from the group consisting of cancer, atherosclerosis, restenosis, inflammatory diseases selected from the group consisting of psoriasis, and autoimmune diseases selected from the group consisting of rheumatoid arthritis.

* * * * *